US012564386B2

(12) United States Patent
Ogawa et al.

(10) Patent No.: US 12,564,386 B2
(45) Date of Patent: Mar. 3, 2026

(54) PROCESSING APPARATUS AND CONTROL METHOD

(71) Applicant: OLYMPUS CORPORATION, Tokyo (JP)

(72) Inventors: Ryohei Ogawa, Kokubunji (JP); Hidetoshi Nishimura, Koganei (JP); Mariko Otagiri, Sagamihara (JP); Yuji Sakamoto, Tokyo (JP); Nao Inoue, Isehara (JP); Shohei Hemmi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 36 days.

(21) Appl. No.: 18/629,500

(22) Filed: Apr. 8, 2024

(65) Prior Publication Data

US 2024/0335185 A1     Oct. 10, 2024

Related U.S. Application Data

(60) Provisional application No. 63/458,220, filed on Apr. 10, 2023.

(51) Int. Cl.
    *A61B 10/04*         (2006.01)
    *A61B 8/00*          (2006.01)
         (Continued)

(52) U.S. Cl.
    CPC ................. *A61B 8/54* (2013.01); *A61B 8/12* (2013.01); *A61B 8/445* (2013.01); *A61B 10/04* (2013.01);
         (Continued)

(58) Field of Classification Search
    CPC .. A61B 8/54; A61B 8/12; A61B 8/445; A61B 10/04; A61B 17/3403;
         (Continued)

(56)            References Cited

U.S. PATENT DOCUMENTS

2003/0078502 A1     4/2003   Miyaki et al.
2019/0247127 A1*    8/2019   Kopel ...................... A61B 6/12
                    (Continued)

FOREIGN PATENT DOCUMENTS

JP         2006346477 A     12/2006
JP         2022550848 A     12/2022
                    (Continued)

OTHER PUBLICATIONS

Extended European Search Report dated Jul. 31, 2024 received in 24163819.6.
                    (Continued)

*Primary Examiner* — Amal Aly Farag
(74) *Attorney, Agent, or Firm* — Scully, Scott, Murphy & Presser, P.C.

(57)            ABSTRACT

Systems and methods for an endoscope system are described. The endoscope system can include a processing apparatus including a processor including hardware. The processor can acquire structure data of an organ, acquire an endoscope image from an imager of an endoscope, and acquire an ultrasonic image from a probe of the endoscope. The processor can automatically control a probe position of the endoscope based on the structure data and the distal end position information of the endoscope in a first control mode, and automatically controls the probe position based on the ultrasonic image in a second control mode.

20 Claims, 28 Drawing Sheets

(51) Int. Cl.
    *A61B 8/12*         (2006.01)
    *A61B 17/34*      (2006.01)

(52) U.S. Cl.
    CPC .... *A61B 17/3403* (2013.01); *A61B 2010/045*
        (2013.01); *A61B 2017/3413* (2013.01)

(58) Field of Classification Search
    CPC ...... A61B 2010/045; A61B 2017/3413; A61B
        1/000094; A61B 1/00098; A61B 1/00133;
          A61B 1/0016; A61B 8/0841; A61B
                    8/4416; A61B 8/4494
    See application file for complete search history.

(56)            References Cited

U.S. PATENT DOCUMENTS

2019/0357883 A1 * 11/2019 Steinberg ............... A61B 10/04
2020/0078103 A1    3/2020 Duindam et al.
2020/0360100 A1 * 11/2020 Mantri ................... A61B 90/37
2021/0259660 A1    8/2021 Bharat et al.
2022/0361858 A1   11/2022 Forsvall et al.
2024/0307127 A1    9/2024 Inagaki et al.

FOREIGN PATENT DOCUMENTS

WO     2021019851 A1   2/2021
WO     2022/059197 A1  3/2022

OTHER PUBLICATIONS

Japanese Office Action dated May 28, 2024 received in 2023-189263.

* cited by examiner

DETERMINE ANGLE
OF BIOPSY NEEDLE

F33

F32

PROCESSING APPARATUS AND CONTROL METHOD

CROSS REFERENCE TO RELATED APPLICATIONS

This application is based upon and claims the benefit of priority to U.S. Provisional Patent Application No. 63/458,220 filed on Apr. 10, 2023, the entire contents of which are incorporated herein by reference.

BACKGROUND

A method of automatically controlling a medical device such as an endoscope using a robot arm or the like has been known. The specification of International Publication No. 2022/059197 discloses a method of constructing a virtual three-dimensional shape image of a subject and acquiring distal end position data of an endoscope to give support to bring the medical device close to a desired position regarding a lesion.

SUMMARY

An aspect of the present disclosure relates to a processing apparatus comprising:
a processor comprising hardware, the processor being configured to:
acquire structure data of an organ;
acquire an endoscope image from an imager of an endoscope;
acquire an ultrasonic image from a probe of the endoscope;
automatically control a probe position of the endoscope based on the structure data and distal end position information of the endoscope in a first control mode; and
automatically control the probe position based on the ultrasonic image in a second control mode.
Another aspect of the present disclosure relates to a control method comprising: acquiring structure data of an organ;
acquiring an endoscope image from an imager of an endoscope;
acquiring an ultrasonic image from a probe of the endoscope;
automatically controlling a probe position of the endoscope based on the structure data and distal end position information of the endoscope in a first control mode; and
automatically controlling the probe position based on the ultrasonic image in a second control mode.

BRIEF DESCRIPTION OF THE DRAWINGS

FIG. 30 is a diagram describing a notification example of the third notification.

DETAILED DESCRIPTION

Figure 1:
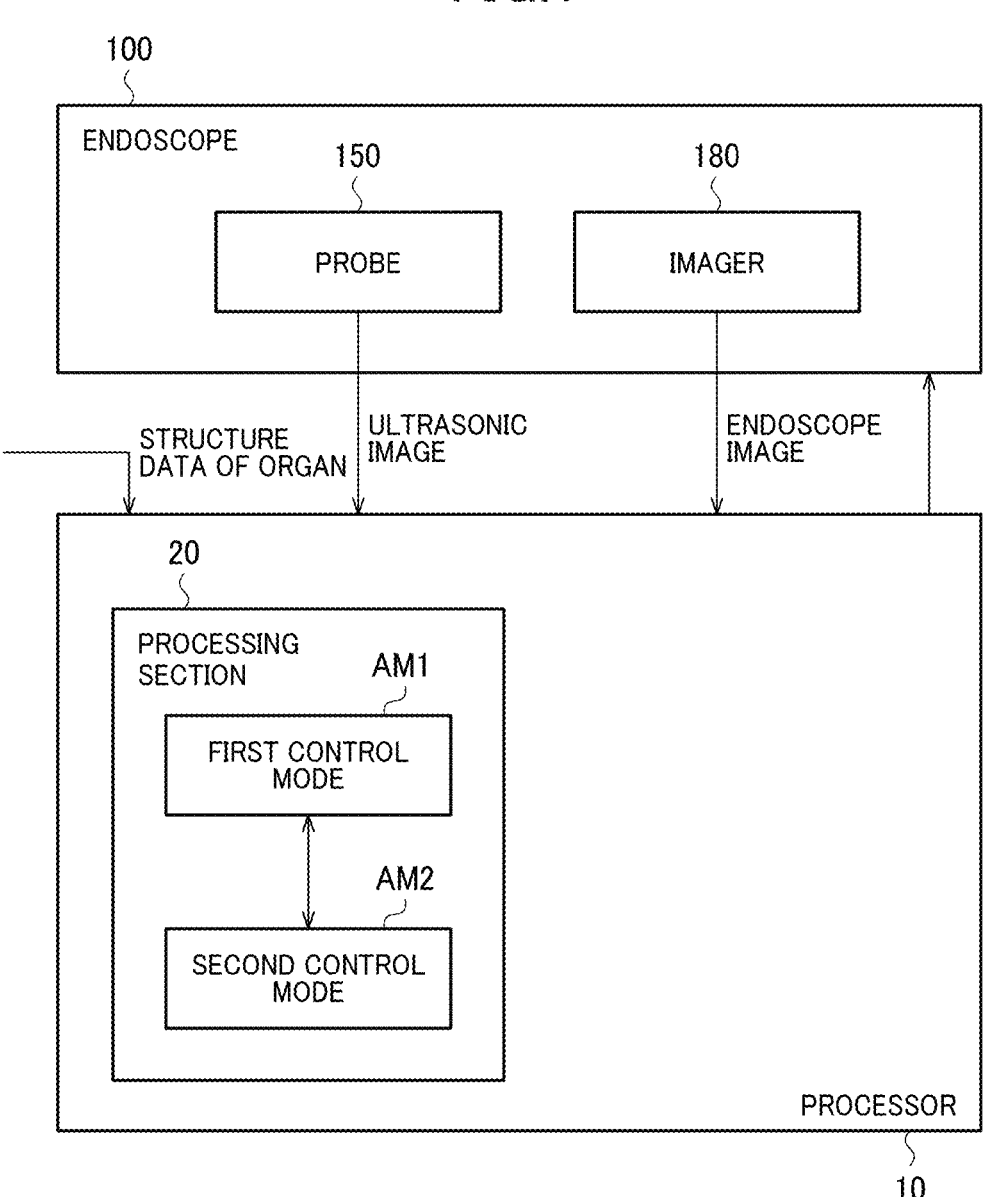
FIG. 1 is a diagram for describing a configuration example of an endoscope system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

A configuration example of an endoscope system 1 according to the present embodiment is described with reference to FIG. 1. As described later in detail, the endoscope system 1 that makes an ultrasonic diagnosis of the inside of the body of a subject using an endoscope 100 as an ultrasonic endoscope and that functions as a medical ultrasonic endoscope system is given as an example in the present embodiment, but the whole or part of a method according to the present embodiment may be applied to, for example, an endoscope without an ultrasonic diagnosis function, an industrial endoscope, or the like. The subject is, for example, a patient, but a main subject that is subjected to an ultrasonic diagnosis is collectively expressed as the subject in the present embodiment. In the following description, a convergent beam of ultrasonic waves used in the ultrasonic diagnosis is simply referred to as ultrasonic waves or a beam. A type of the endoscope 100 to which the method according to the present embodiment is applied is exemplified by a convex-type ultrasonic endoscope based on a scan method for performing scan along a convex surface with a beam, but the method according to the present embodiment is not prevented from being applied to a sector-type ultrasonic endoscope, a linear-type ultrasonic endoscope, a radial-type ultrasonic endoscope, or the like. Note that the convex-type ultrasonic endoscope will be described later with reference to FIGS. 2 and 3.

The endoscope system 1 according to the present embodiment includes a processor 10. The processor 10 according to the present embodiment has the following hardware configuration. The hardware can include at least one of a circuit that processes a digital signal or a circuit that processes an analog signal. For example, the hardware can include one or more circuit devices mounted on a circuit board, or one or more circuit elements. The one or more circuit devices are, for example, integrated circuits (ICs) or the like. The one or more circuit elements are, for example, resistors, capacitors, or the like.

For example, the endoscope system 1 according to the present embodiment may include a memory 12, which is not illustrated in FIG. 1, and the processor 10 that operates based on information stored in the memory 12. With this configuration, the processor 10 can function as a processing section 20. The information is, for example, a program, various kinds of data, and the like. Note that the program may include, for example, a trained model 22, which will be described later with reference to FIG. 17. A central processing unit (CPU), a graphics processing unit (GPU), a digital signal processor (DSP), or the like can be used as the processor 10. The memory 12 may be a semiconductor memory such as a static random access memory (SRAM) and a dynamic random access memory (DRAM). The memory 12 may be a register. The memory 12 may be a magnetic storage device such as a hard disk device. The memory 12 may be an optical storage device such as an optical disk device. For example, the memory 12 stores a computer-readable instruction. The instruction is executed by the processor 10, whereby functions of sections of the processing section 20 are implemented. The instruction mentioned herein may be an instruction set that is included in the program, or may be an instruction that instructs the hardware circuit included in the processor 10 to operate. The memory 12 is also referred to as a storage device. The main section that performs processing or the like according to the present embodiment is collectively referred to as the processor 10 unless otherwise described, but can be replaced by the processing section 20 as software as appropriate.

As illustrated in FIG. 1, the processor 10 acquires structure data of an organ, which will be described later. The processor 10 acquires an endoscope image from an imager 180 of the endoscope 100, and acquires an ultrasonic image from a probe 150 of the endoscope 100. The probe 150 is included in a distal end portion 130 of the endoscope 100. The distal end portion 130 will be describe later with reference to FIG. 2. The imager 180 cannot be visually recognized in FIG. 2, but is included in the distal end portion 130 of the endoscope 100 similarly to the probe 150.

The processor 10 is capable of automatically controlling a position of the probe 150 with a first control mode AM1 or a second control mode AM2, which will be described later. That is, the memory 12, which is not illustrated in FIG. 1, includes a program to automatically control the endoscope 100 in the first control mode AM1, a program to automatically control the endoscope 100 in the second control mode AM2, and a program to switch between the first control mode AM1 and the second control mode AM2. The processor 10 reads out and executes these programs, as necessary. In the following description, the position of the probe 150 may be simply expressed as a probe position.

The automatic control mentioned herein in the present embodiment is that the processor 10, instead of a user, makes determination and controls each section regarding the endoscope system 1, that is, the processor 10 controls each section that is connected to the endoscope system 1 using a predetermined control algorithm. The user mentioned herein is a main person who handles the endoscope system 1, and can be also referred to as an operator, but is collectively expressed as the user in the following description. Each section regarding the endoscope system 1 mentioned herein is the endoscope 100, each section of the endoscope 100, a treatment tool 400, an endoscope observation device, an ultrasonic observation device, a light source device, an air supply/water supply device, or the like. The ultrasonic observation device, the light source device, and the air supply/water supply device are not illustrated. That is, the endoscope system 1 according to the present embodiment is assumed to a medical system in which the endoscope 100 is motorized. The motorization of the endoscope 100 mentioned herein is, for example, the motorization of the endoscope 100 itself, but includes an operation of a non-motorized endoscope 100 by a motorized robot arm or the like.

The motorization mentioned herein means that the endoscope 100 is driven by an actuator such as a motor based on an electric signal for controlling the operation of the endoscope 100. In contrast, the non-motorization mentioned herein means that the endoscope 100 is operated, instead of by being electrically driven by a motor or the like, by direct transmission of force applied to an operation section to the endoscope 100 through a wire or the like. For example, in a case of a non-motorized operation of the endoscope 100, the endoscope 100 is manually operated by the user. The case where the endoscope 100 is motorized may include not only a case where the endoscope 100 is electrically driven at the processor 10's determination, but also a case where the endoscope 100 is electrically driven by the user's manual operation of the operating section, which is not illustrated. That is, in the present embodiment, each of the first control mode AM1 and the second control mode AM2 is a control mode for electrically driving the endoscope 100 at processor 10's determination, and a manual control mode MM, which will be described later, is a control mode for electrically driving the endoscope 100 in response to the user's manual operation of the operation section, which is not illustrated, in every treatment.

In addition, each of the first control mode AM1 and the second control mode AM2 includes a full-automatic mode and a semi-automatic mode, which will be described later, and the full-automatic mode and the semi-automatic mode may be switched as appropriate. The full-automatic mode is a control mode in which the endoscope 100 is automatically controlled by the processor 10 in every treatment and the user's manual operation is not accepted or is disabled. A route of the distal end portion 130 and an operation procedure of the endoscope 100 are programmed based on present position information of the distal end portion 130 of the endoscope 100 and position information of a destination, and the processor 10 reads out and executes the program, and thereby electrically drives the endoscope 100 to move the endoscope 100 to a set position of the destination. Alternatively, for example, the processor 10 may electrically control the endoscope 100 based on a result of processing using machine learning. The semi-automatic mode is an operation mode in which the endoscope 100 is normally electrically driven by the user's manual operation, but automatic control of the endoscope 100 by the processor 10 intervenes under a predetermined condition. For example, when the distal end portion 130 is expected to come in contact with the intestinal wall of the duodenum as the predetermined condition, the processor 10 performs automatic control to avoid the contact. For example, when the distal end portion 130 is expected to come in contact with the intestinal wall of the duodenum in a state where a curved portion 102 is curved, the processor 10 automatically controls a curving operation, and can thereby avoid the contact. Note that the processor 10 may automatically control an advance/retreat operation, which is an operation other than the curving operation, so as to be able to avoid the contact.

In the present embodiment, in a case where the endoscope 100 operates in a non-motorized manner in part of treatments, the endoscope 100 may be regarded as being motorized. For example, as described later, in the endoscope system 1 according to the present embodiment, each of advance/retreat of an insertion portion 110 of the endoscope 100, curving of the curved portion 102, and roll rotation is motorized, but the endoscope 100 may be regarded as being motorized only if an operation of at least one of these devices is motorized.

The endoscope 100 according to the present embodiment uses the probe 150 to convert electric pulse-type signals received from the ultrasonic observation device, which is not illustrated, into pulse-type ultrasonic waves using the probe 150, irradiate the subject with the ultrasonic waves, convert the ultrasonic waves reflected by the subject into echo signals, which are electric signals expressed by a voltage change, and output the echo signals to the processor 10. For example, the endoscope 100 transmits the ultrasonic waves to tissues around a digestive tract or a respiratory organ, and receives the ultrasonic waves reflected on the tissues. The digestive tract is, for example, the esophagus, the stomach, the duodenum, the large intestine, or the like. The respiratory organ is, for example, the trachea, the bronchus, or the like. The issue is, for example, the pancreas, the gallbladder, the bile duct, the bile duct tract, lymph nodes, a mediastinum organ, blood vessels, or the like. The ultrasonic observation device, which is not illustrated, performs predetermined processing on the echo signals received from the probe 150 to generate ultrasonic image data. The predetermined processing mentioned herein is, for example, bandpass filtering, envelope demodulation, logarithm transformation, or the like.

The imager 180 can also be referred to as a camera, includes an image sensor, an optical member, or the like, and functions as an imaging device. The image sensor includes a charge-coupled device (CCD), a complementary metal-oxide semiconductor (CMOS) sensor, or the like. With this configuration, the imager 180 is inserted into the digestive tract or respiratory organ of the subject, and is capable of capturing an image of the digestive tract, the respiratory organ, or the like. In the present embodiment, an image captured by the imager 180 is referred to as an endoscope image. The endoscope image may be a still image from a video image captured by the imaging section.

Although not illustrated in FIG. 1, the endoscope 100 according to the present embodiment can include the treatment tool 400. For example, a treatment tool insertion path is arranged inside the insertion portion 110, which will be described later, and an insertion opening 190, which will be described later, is connected to the treatment tool insertion path. With this configuration, the treatment tool 400 inserted from the insertion opening 190 is led out from a distal end opening portion 134, which will be described later with reference to FIG. 2, via the treatment tool insertion path. In the following description, a biopsy needle 410 is given as an example of the treatment tool 400 and Endoscopic Ultra-Sound-guided Fine Needle Aspiration (EUS-FNA) is given as a manipulation to use the biopsy needle 410, but another treatment tool 400 is not prevented from being applied to the endoscope system 1 according to the present embodiment, and the method according to the present embodiment is not prevented from being applied to a manipulation other than the EUS-FNA. The EUS-FNA is an abbreviation for Endoscopic UltraSound-guided Fine Needle Aspiration. Since the EUS-FNA is a treatment performed by the user to avoid a region that should not be damaged and project the biopsy needle 410 while watching the ultrasonic image, it is important to arrange the probe 150 at an appropriate position.

A configuration example of the distal end portion 130 of the endoscope 100 will be described with reference to FIGS. 2 to 4. Note that the configuration of each portion of the distal end portion 130 according to the present embodiment is not limited to the following description, and can be modified in various manners. As a matter of descriptive convenience, X, Y, and Z axes are illustrated as three axes that are orthogonal to each other in FIGS. 3 and 4. A direction along the X axis is referred to as an X axis direction, and is a direction along a longitudinal direction of the distal end portion 130. Assume that a distal end side is a +X direction, and a base end side is a −X direction. A direction along the Y axis is referred to as a Y axis direction, and a direction along the Z axis is referred to as a Z axis direction. In a case where an ultrasonic diagnosis is performed using an ultrasonic transducer array 155 in a one-dimensional array, which is exemplified in FIG. 3, each of the X axis direction, the Y axis direction, and the Z axis direction in FIGS. 2 and 3 can also be referred to as a scanning direction, a slice direction, and a distance direction. Assume that being "orthogonal" includes, in addition to being orthogonal at 90°, a case of being orthogonal at an angle somewhat inclined from 90°.

Figure 2:
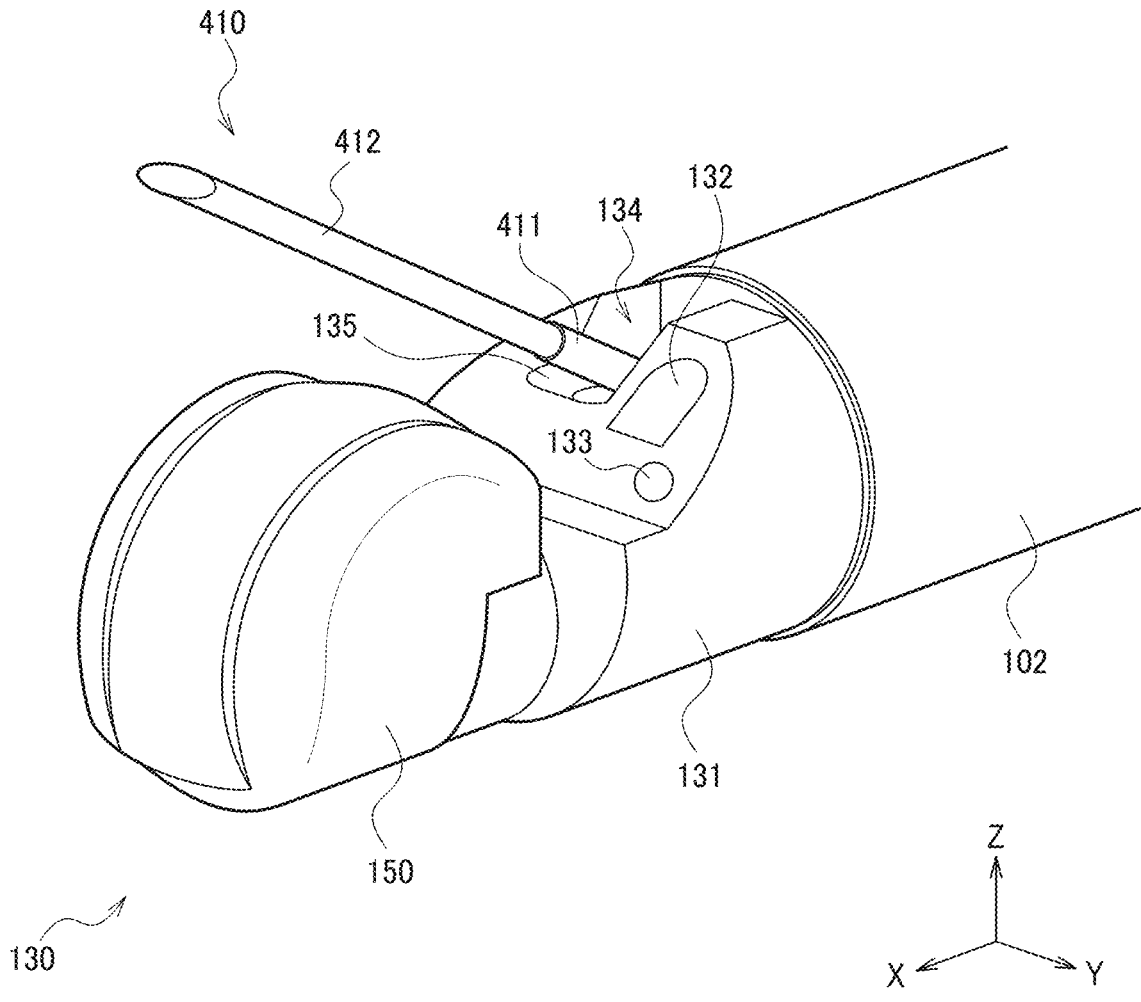
FIG. 2 is a diagram for describing a configuration example of a distal end portion.

As illustrated in a perspective view in FIG. 2, the distal end portion 130 includes a main portion 131 and the probe 150 that projects toward the distal end side of the main portion 131. The main portion 131 includes an objective lens 132, an illumination lens 133, and the distal end opening portion 134. The objective lens 132 constitutes part of the imager 180, and captures light from the outside. The illumination lens 133 condenses illumination light and emits the illumination light to the outside. The illumination light according to the present embodiment may include predetermined pattern light, which will be described later. The distal end opening portion 134 is an outlet of the treatment tool insertion path, which will be described later. Although not illustrated in FIG. 2, the distal end portion 130 may additionally include an air supply/water supply nozzle or the like, although the air supply/water supply nozzle is not illustrated in FIG. 2. FIG. 2 illustrates one objective lens 132 and one illumination lens 133, but there may be two or more objective lenses 132 and two or more illumination lenses 133.

The probe 150 and a raising base 135 are now described with reference to FIG. 3. In FIG. 3, a configuration necessary for description is added to a cross-sectional view at the center of the distal end portion 130 in the Y axis direction as appropriate, and a configuration that is unnecessary for description is deleted as appropriate for descriptive convenience. As illustrated in FIG. 3, the raising base 135 is arranged in the distal end opening portion 134 of the main portion 131. FIG. 3 illustrates that, at a basic position of the raising base 135, the longitudinal direction of the raising base 135 is not matched with the longitudinal direction of the distal end portion 130, and is inclined by an angle indicated by R1 from a longitudinal axis of the distal end portion 130. However, for example, at the basic position of the raising base 135, the longitudinal direction of the raising base 135 and the longitudinal direction of the distal end portion 130 may be parallel. Being parallel mentioned herein includes being substantially parallel, and the same applies to the following description. The longitudinal axis of the distal end portion 130 is an axis along the longitudinal direction of the distal end portion 130, and is an axis that is parallel to the X axis illustrated in FIG. 3 or the like. In the present embodiment, assume that a projection direction of the biopsy needle 410 can be regarded as being parallel to the longitudinal direction of the raising base 135. That is, in FIG. 3, the direction in which the biopsy needle 410 projects based on the basic position of the raising base 135 is inclined by the angle indicated by R1 from the longitudinal axis of the distal end portion 130. In the following description, an angle formed between the longitudinal direction of the raising base 135 and the longitudinal direction of the distal end portion 130 is hereinafter referred to as an inclination angle of the raising base 135. In addition, an angle in the projection direction of the biopsy needle 410 based on the longitudinal direction of the distal end portion 130 is simply referred to as an angle of the biopsy needle 410. That is, since the angle of the biopsy needle 410 is identical to the inclination angle of the raising base 135, the endoscope system 1 performs measurement or the like of the inclination angle of the raising base 135, and can thereby grasp the angle of the biopsy needle 410.

A raising base operation wire 136 is connected to the raising base 135. The user operates a raising base operation section, which is not illustrated, whereby the raising base operation wire 136 is pulled in a direction indicated by B11. As a result, the inclination angle of the raising base 135 changes in a direction indicated by B12. This allows the user to adjust a led-out angle of the biopsy needle 410. The raising base operation section, which is not illustrated, is included in, for example, an operation device 300 or the like. In the case of FIG. 3, the user operates the raising base operation section, which is not illustrated, whereby the inclination angle of the raising base 135 changes to be an angle larger than the angle indicated by R1.

The endoscope system 1 according to the present embodiment may be capable of grasping the inclination angle of the raising base 135. For example, the endoscope system 1 measures the inclination angle of the raising base 135 with an angle sensor, which is not illustrated, and can thereby grasp the inclination angle of the raising base 135. Alternatively, the endoscope system 1 may measure an operation amount of the raising base operation wire 136 using a sensor, which is not illustrated, and use a first table that associates the operation amount of the raising base operation wire 136 and the inclination angle of the raising base 135 with each other to grasp the inclination angle of the raising base 135. The raising base operation section, which is not illustrated, may be configured to control a stepping motor that pulls the raising base operation wire 136, and a table that associates the number of steps of the stepping motor and the inclination angle of the raising base 135 may serve as the first table. With this configuration, the endoscope system 1 is capable of grasping the inclination angle of the raising base 135, that is, the angle of the biopsy needle 410 in association with control of the raising base operation wire 136.

Figure 3:
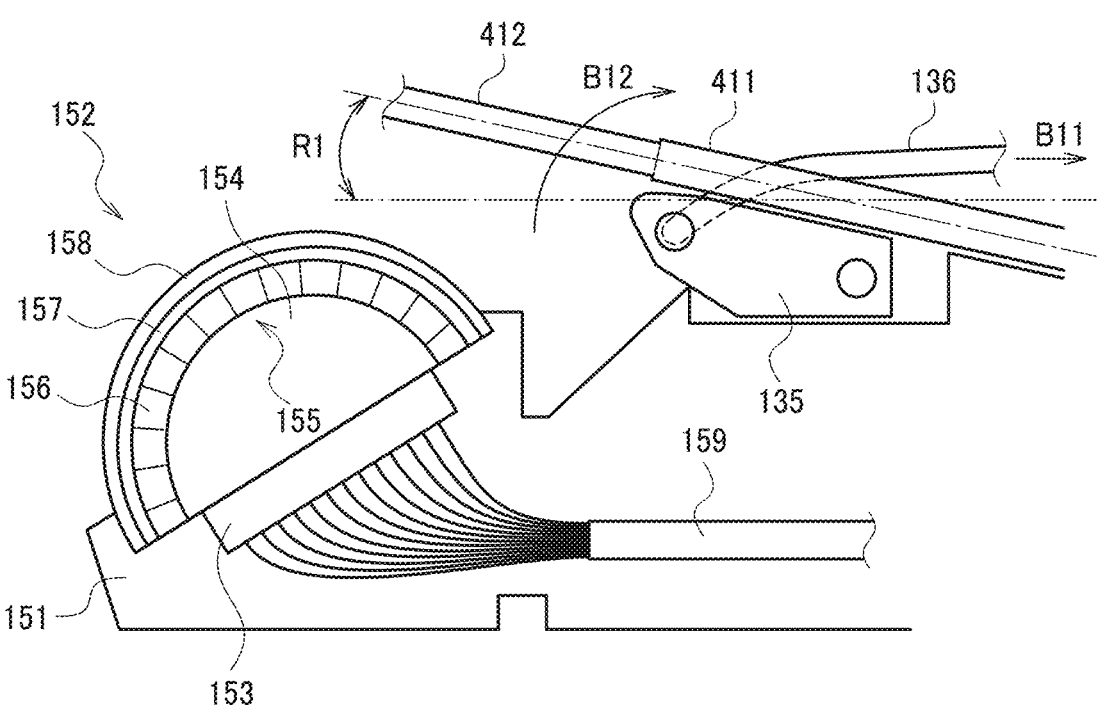
FIG. 3 is a diagram for describing an example of a probe and a raising base of a treatment tool.
Figure 3:
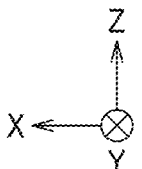

The probe 150 includes a housing 151 and an ultrasonic transducer unit 152, as illustrated in FIG. 3. The ultrasonic transducer unit 152 is engaged with the housing 151 and fixed. The ultrasonic transducer unit 152 includes a wiring substrate 153, a backing material 154, the ultrasonic transducer array 155, an acoustic matching layer 157, and an acoustic lens 158. The ultrasonic transducer array 155 includes a plurality of ultrasonic transducers 156. The ultrasonic transducer unit 152 having the above-mentioned configuration functions as the probe 150. Although not illustrated, in a case where an internal space exists in the housing 151, the ultrasonic transducer unit 152 may further include a filling portion that fills the internal space. For the filling portion, a material that is identical to the backing material 154 may be used, or another member having a heat dissipation property may be used.

The wiring substrate 153 functions as a relay substrate that relays the ultrasonic observation device, which is not illustrated, and the ultrasonic transducer array 155. That is, the wiring substrate 153 is electrically connected to each wire included in an ultrasonic cable 159 via an electrode, which is not illustrated, and is electrically connected to the corresponding ultrasonic transducer 156 via an electrode, which is not illustrated, a signal line, or the like. The wiring substrate 153 may be a rigid substrate or a flexible substrate.

The backing material 154 mechanically supports the ultrasonic transducer array 155, and also attenuates ultrasonic waves that propagate from the ultrasonic transducer array 155 to the inside of the probe 150. The backing material 154 is formed of, for example, a material having rigidity such as hard rubber, or the material may further contain ferrite, ceramic, or the like to form the backing material 154. This configuration can effectively attenuate ultrasonic waves that propagate to the inside of the probe 150.

The ultrasonic transducer array 155 is configured so that the plurality of ultrasonic transducers 156 is arrayed at regular intervals in a one-dimensional array to form a convex curve shape along the X axis direction. The ultrasonic transducers 156 that constitute the ultrasonic transducer array 155 can be implemented by, for example, a piezoelectric element formed of piezoelectric ceramic represented by lead zirconate titanate (PZT), a piezoelectric polymer material represented by polyvinylidene difluoride (PVDF), or the like. In each ultrasonic transducer 156, a first electrode and a second electrode, which are not illustrated, are formed. The first electrode is electrically connected to the corresponding wire of the ultrasonic cable 159 via a signal line or the like on the wiring substrate 153. The signal line is not illustrated. The second electrode is connected to a ground electrode on the wiring substrate 153. The ground electrode is not illustrated. With this configuration, the ultrasonic transducers 156 can be sequentially driven based on a drive signal input by an electronic switch such as a multiplexer. With this configuration, the piezoelectric elements that constitute the ultrasonic transducers 156 are oscillated, whereby ultrasonic waves can be sequentially generated. In the ultrasonic transducer array 155, for example, the plurality of ultrasonic transducers 156 may be arrayed in a two-dimensional array, and ultrasonic transducer array 155 can be modified in various manners.

The acoustic matching layer 157 is laminated outside the ultrasonic transducer array 155. A value of acoustic impedance of the acoustic matching layer 157 is within a range between a value of acoustic impedance of the ultrasonic transducer 156 and a value of acoustic impedance of the subject. This configuration allows ultrasonic waves to effectively penetrate the subject. The acoustic matching layer 157 is formed of, for example, an organic material such as an epoxy resin, a silicon rubber, polyimide, and polyethylene. Note that the acoustic matching layer 157 is illustrated as one layer for convenience in FIG. 3, but may include a plurality of layers.

The acoustic lens 158 is arranged outside the acoustic matching layer 157. The acoustic lens 158 reduces friction with the stomach wall or the like against which the probe 150 is pressed, and also reduces a beam diameter in the Y axis direction of a beam transmitted from the ultrasonic transducer array 155. This configuration enables vivid display of an ultrasonic image. The acoustic lens 158 is formed of, for example, a silicon-based resin, a butadiene-based resin, or a polyurethane-based resin, but may be formed by further containing powder of oxidized titanium, alumina, silica, or the like. A value of acoustic impedance of the acoustic lens 158 is within a range between the value of acoustic impedance of the acoustic matching layer 157 and the value of acoustic impedance of the subject.

The biopsy needle 410 includes a sheath portion 411, and a needle portion 412 that is inserted through the inside of the sheath portion 411. The sheath portion 411 includes, for example, a coil-shaped sheath, and has flexibility. The length of the sheath portion 411 can be adjusted as appropriate according to the length of the insertion portion 110. The needle portion 412 is formed of, for example, a nickel-titanium alloy or the like, and the distal end thereof is processed to be sharp. This allows the needle portion 412 to be inserted into a hard lesion. In addition, surface processing such as sandblast processing and dimple processing may be performed on the surface of the needle portion 412. With this configuration, it becomes possible to further reflect ultrasonic waves on the surface of the needle portion 412. This allows the needle portion 412 to be clearly displayed in the ultrasonic image, which will be described later. Note that the lesion mentioned herein is a portion that is considered to be in a state different in appearance from a normal state, and is not necessarily limited to a portion that attributes to a disease. That is, the lesion is, for example, a tumor, but is not limited thereto, and may be a polyp, an inflammation, a diverticulum, or the like.

Although not illustrated, various configurations of the needle portion 412 have been proposed, and any configurations may be applied to the biopsy needle 410 that is used in the endoscope system 1 according to the present embodiment. For example, the needle portion 412 includes a cylinder needle and a stylet that is inserted through the inside of a cylinder of the needle. At least one of a distal end of the needle or a distal end of the stylet has a sharp shape, for example, but one needle may constitute the needle portion 412. Note that the needle may be referred to as an outer needle or the like. In addition, the stylet may be referred to as an inner needle or the like. In any configurations of the needle portion 412, it is possible to make a predetermined space for collecting cellular tissues regarding the lesion. The cellular tissues regarding the lesion are taken into the predetermined space.

For example, the user inserts the biopsy needle 410 from the insertion opening 190 in a state where the needle portion 412 is housed in the sheath portion 411. As the user inserts the biopsy needle 410, a first stopper mechanism that is located at a predetermined position on the base end side of the distal end opening portion 134 comes into contact with the distal end of the sheath portion 411. The first stopper mechanism is not illustrated. This prevents the sheath portion 411 from moving from the predetermined position toward the distal end side. Alternatively, a mechanism for stopping the advance of the sheath portion 411 on the base end side of the insertion opening 190 may be arranged and serve as the first stopper mechanism. With this state of the sheath portion 411, the user uses a first slider, which is not illustrated, to project only the needle portion 412 from the distal end side of the sheath portion 411. In a case where the needle portion 412 includes the needle and the stylet, the user may be able to project the needle portion 412 in a state where the needle and the stylet are integrated with each other. With this configuration, as illustrated in FIG. 4, the needle portion 412 projects from the distal end opening portion 134. Alternatively, for example, only the stylet may be retreated with use of a second slider without a change of the position of the needle. The second slider is not illustrated. This enables formation of a space between the needle and the stylet. The space will be described later.

Note that the above-mentioned slider mechanism of the needle portion may further include a second stopper mechanism so as to be capable of adjusting a maximum stroke amount of the needle portion 412. The maximum stroke amount of the needle portion 412 is a maximum projectable length of the needle portion 412 from the sheath portion 411. This can prevent the needle portion 412 from excessively projecting from the sheath portion 411.

Figure 11:
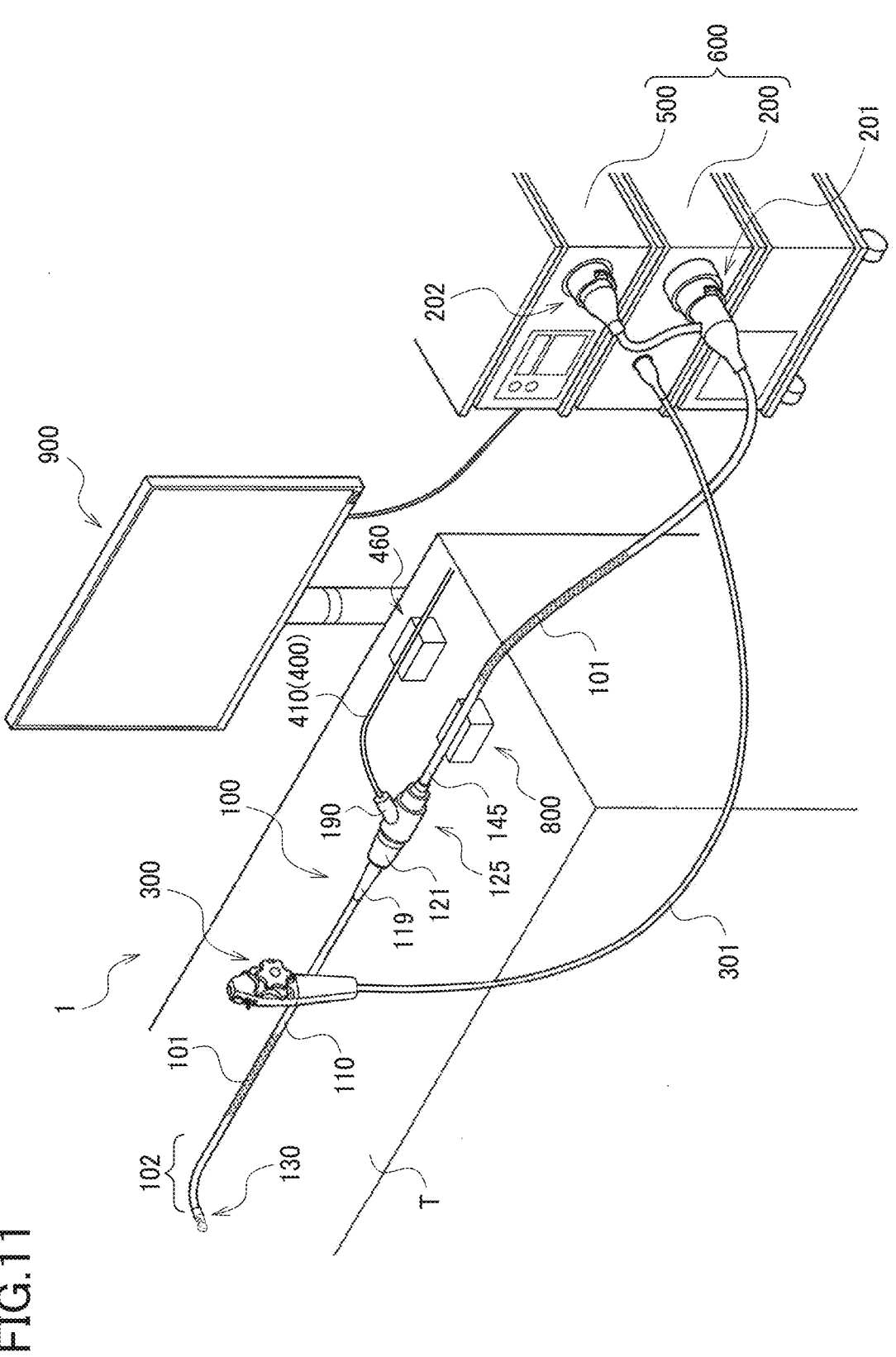
FIG. 11 is a diagram for describing a configuration example of a motorized endoscope system.

In the above-mentioned treatment of the EUS-FNA, each portion that constitutes the biopsy needle 410 can be manually advanced/retreated by the user, but the biopsy needle 410 may be capable of advancing/retreating in a motorized manner, which will be described in detail later with reference to FIG. 11 or the like.

The user uses the endoscope 100 including the distal end portion 130 having the above-mentioned configuration, whereby the endoscope system 1 acquires the ultrasonic image. While the ultrasonic image in a brightness mode (B mode) will be given as an example in the following description, this does not prevent the endoscope system 1 according to the present embodiment from being capable of further displaying the ultrasonic image in another mode. The other mode is, for example, an amplitude mode (A mode), a coronal mode (C mode), a motion mode (M mode), or the like.

The B mode is a display mode for converting amplitude of ultrasonic waves to luminance and display a tomographic image. An upper center portion of the ultrasonic image is a region corresponding to the probe 150. For example, as illustrated in an upper stage of FIG. 4, scan is performed with ultrasonic waves in a scan range along a curved surface of the probe 150, for example, in a range at a predetermined distance from the center of curvature of the curved surface. In a case where the projecting biopsy needle 410 is included in the scan range, for example, an ultrasonic image indicated by C0 is drawn so as to include an image corresponding to the biopsy needle 410 indicated by C1.

Figure 4:
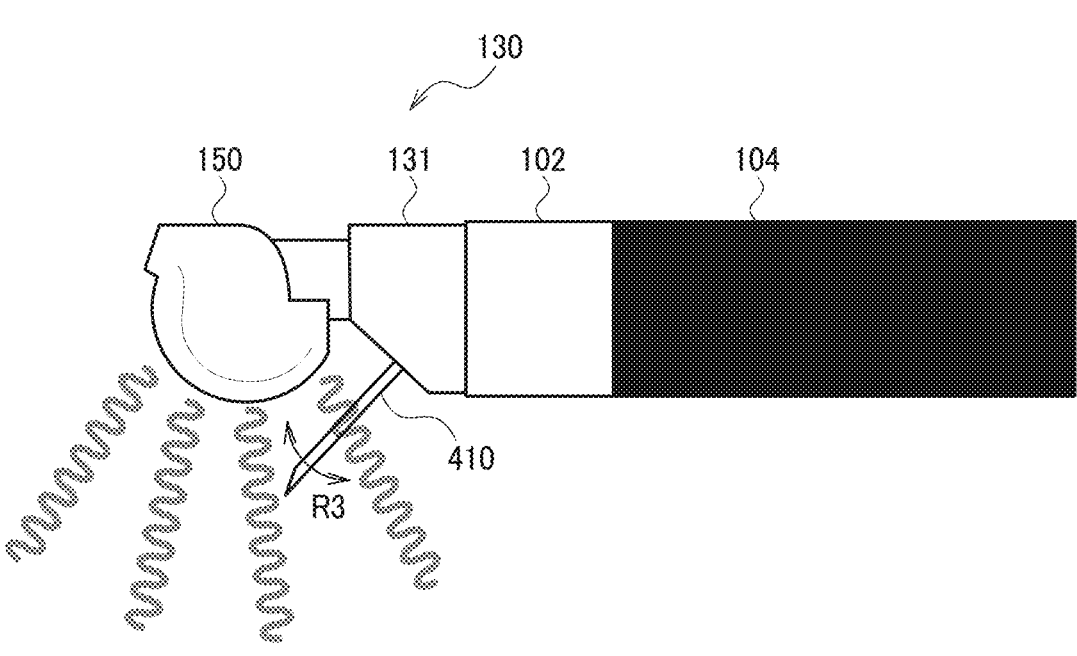
FIG. 4 is a diagram for describing a relationship between an ultrasonic image and a movable range of a biopsy needle.
Figure 4:
Figure 4:
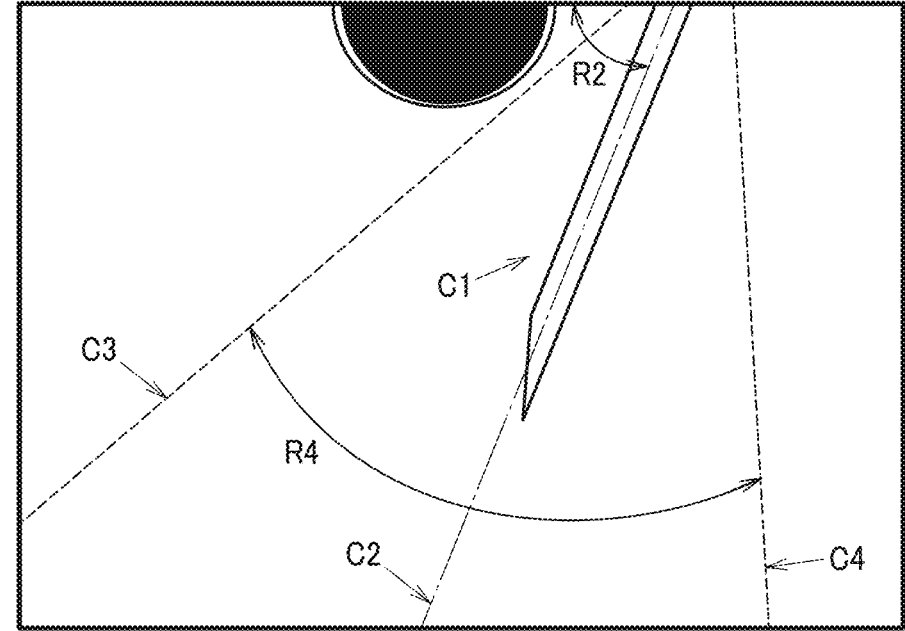

While an actual ultrasonic image is a grayscale image, FIG. 4 schematically illustrates an image corresponding to the biopsy needle 410 and an image regarding region marker information, which will be described later, and other images are omitted for descriptive convenience. The ultrasonic image in FIG. 4 is displayed so that the left side of the image is the distal end side, the right side of the image is the base end side, and the upper center of the image is the curved surface of the probe 150. The same applies to ultrasonic images which are subsequently illustrated.

Since the longitudinal direction of the biopsy needle 410 is not matched with the longitudinal direction of the distal end portion 130 as described above with reference to FIG. 3, the image corresponding to the biopsy needle 410 is displayed in the ultrasonic image so as to be inclined by an angle indicated by R2 from the right side on the upper side of the ultrasonic image. The angle indicated by R2 in FIG. 4 corresponds to the angle indicated by R1 and described with reference to FIG. 3, that is, the angle of the biopsy needle 410. In other words, the angle indicated by R2 in FIG. 4 is the angle of the biopsy needle 410 on the ultrasonic image. Since the image processing is performed, the angle indicated by R2 in FIG. 4 is not necessarily matched with the inclination angle of the raising base 135 indicated by R1 in FIG. 3. To address this, for example, a second table indicating a correspondence relationship between the angle indicated by R1 in FIG. 3 and the angle indicated by R2 in FIG. 4 is stored in the memory 12, and a method of converting the angle of the biopsy needle 410 indicated by R2 on the ultrasonic image using the second table is used, whereby the angle of the biopsy needle 410 on the ultrasonic image can be handled as the actual angle of the biopsy needle 410.

In the present embodiment, for example, a range in which the biopsy needle 410 can be drawn may be shown on the ultrasonic image. A structure of each portion constituting the distal end portion 130 and a range of the inclination angle of the raising base 135 are determined by design as indicated by R3. In addition, a positional relationship between the probe 150 and the distal end opening portion 134 is fixed. Hence, a range of a region in which the biopsy needle 410 is displayed on the ultrasonic image can be preliminarily calculated as indicated by R4. Thus, a movable range image indicating the range is preliminarily stored in the memory 12 and image processing to perform display so as to superimpose the ultrasonic image acquired from the endoscope 100 and the movable range image on each other is performed, whereby display of the movable range image as indicated by C3 and C4 in FIG. 4 can be implemented. An interval between a dotted line indicated by C3 and a dotted line indicated by C4 in FIG. 4 is a range in which the biopsy needle 410 can be displayed on the ultrasonic image. In other words, the movable range image is an image that indicates a contour of a region made of a set of images of the biopsy needle 410 that can be displayed on the ultrasonic image.

Note that the endoscope system 1 may be capable of adjusting a display position of the movable range image. With this configuration, a predetermined error is corrected, and the movable range of the biopsy needle 410 corresponding to the movable range image and the actual movable range of the biopsy needle 410 can be matched with each other with high accuracy. The predetermined error is, for example, an error based on a tolerance in processing of the distal end portion 130, an error based on how the sheath portion 411 of the biopsy needle 410 is curved, or the like. For example, the following method can implement adjustment of the display position of the movable range image.

For example, the user uses a drawing function of a touch panel or another function to perform drawing or the like of a straight line so as to be superimposed on a displayed image of the biopsy needle 410, whereby the endoscope system 1 acquires information of a first straight line based on coordinates on the ultrasonic image as indicated by C2 in FIG. 4. The endoscope system 1 compares the angle of the biopsy needle 410 that is obtained from an inclination of the first straight line and the above-mentioned second table and the angle of the biopsy needle 410 that is grasped based on the above-mentioned angle sensor or the raising base operation wire 136, and performs processing of complementing a value of the second table so that these angles are matched with other. This configuration enables more accurate display of the movable range image. Note that the first straight line indicated by C2 may be displayable as an image. In a case where the inclination angle of the raising base 135 is adjusted while the image of the first straight line is displayed on the ultrasonic image, the image of the first straight line may be rotationally moved in conjunction with the adjustment. In the following description, assume that the movable range image is displayed accurately.

Figure 5:
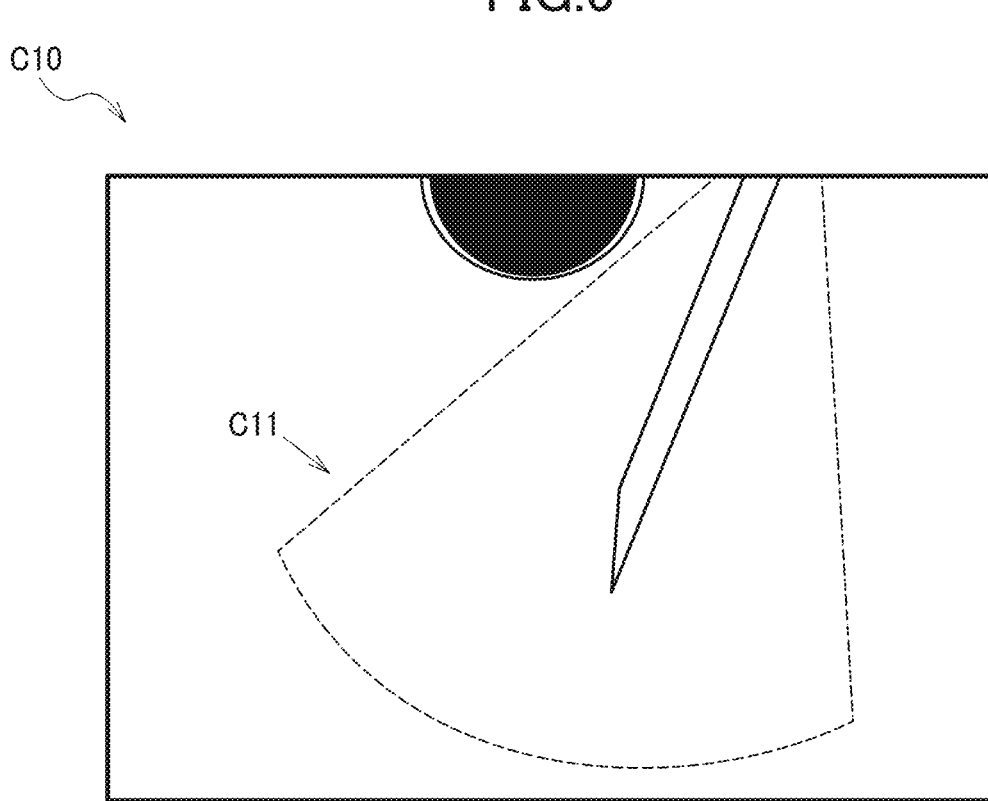
FIG. 5 is another diagram for describing the relationship between the ultrasonic image and the movable range of the biopsy needle.

While the above description has been given of the example of displaying the movable range image based on the angle of the biopsy needle 410, for example, the processor 10 may further calculate a depth of the biopsy needle 410, and display the movable range image based on the angle and depth of the biopsy needle 410. The depth of the biopsy needle 410 is, for example, a projectable length of the needle portion 412 from the distal end of the sheath portion 411. As described above, because the position of the distal end of the sheath portion 411 and the maximum stroke amount of the needle portion 412 are preliminarily known or for other reasons, the maximum length of the needle portion 412 displayed on the ultrasonic image based on the maximum stroke amount of the needle portion 412 can also be calculated together similarly to the case of calculation of the angle of the biopsy needle 410. With this configuration, for example, the movable range image indicated by C11 is displayed as part of an arc-shaped figure in the ultrasonic image indicated by C10 in FIG. 5. Note that the center of the arc is not displayed on the ultrasonic image. This is because the center of the arc corresponds to the position of the distal end opening portion 134, and ultrasonic waves do not reach the position.

Figure 6:
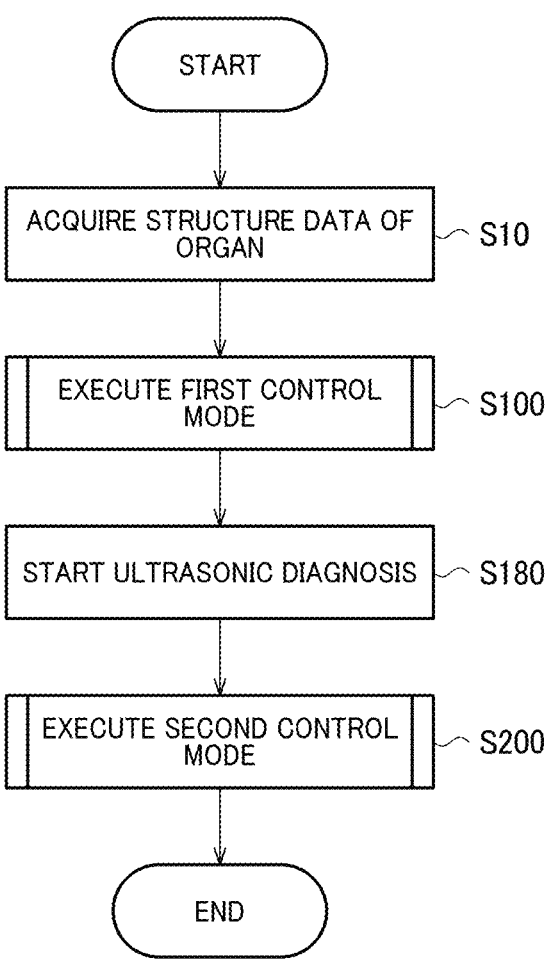
FIG. 6 is a flowchart describing a processing example of a method according to the present embodiment.

FIG. 6 is a flowchart describing a processing example of the method according to the present embodiment. There is a case where each step in FIG. 6 is repeated multiple times. The processor 10 acquires structure data of an organ (step S10). The structure data of the organ is three-dimensional shape information that is re-constructed based on three-dimensional image data of the organ. The three-dimensional image data mentioned herein is image data in which the position of each pixel is defined by a three-dimensional coordinate system, and is, for example, image data captured by a method of computerized tomography (CT), magnetic resonance imaging (MRI), positron emission tomography (PET), or the like. The three-dimensional image data is preliminarily acquired by the above-mentioned method or the like performed on the living body as the subject, and is stored in, for example, the memory 12, which will be described later, a database of an external device, which is not illustrated, or the like. The processor 10 then performs, for example, a method such as volume rendering to reconstruct these pieces of three-dimensional image data as the three-dimensional shape information.

In step S10, the user identifies the position of the lesion as a treatment target in the EUS-FNA with coordinates in a coordinate space based on the structure data of the organ. Note that the coordinate space based on the structure data of the organ may be hereinafter referred to as a first coordinate space for descriptive convenience. The user then uses coordinate information in the first coordinate space to set a target position, which is the position information of the probe 150 and is an appropriate position at which the biopsy needle 410 is inserted into the lesion. More specifically, the position of the probe 150 that satisfies a condition that the lesion is shown on the ultrasonic image acquired by the probe 150 and the biopsy needle 410 can be inserted into the lesion is the target position. Alternatively, the biopsy needle 410 not reaching an important tissue, which will be described later, may be added to the condition.

Thereafter, the processor 10 operates the endoscope 100 in the first control mode AM1 (in step S100). As described later, step S100 is various kinds of processing performed by the processor after control to make a shift to the first control mode AM1, but may be hereinafter simply referred to as the first control mode AM1 (step S100) in the following description or illustration. The same applies the second control mode AM2 (step S200), which will be described later. For example, after a route of the probe 150 and an operation procedure of the endoscope 100 are programmed based on the set target position, the processor 10 executes readout of the program, and thereby electrically drives the endoscope 100 so as move to the set target position. Note that step S100 may be executed in a state where the insertion portion 110, which will be described later, is inserted into an overtube. With this processing, another treatment tool 400 other than the insertion portion 110 can be inserted into the overtube.

Thereafter, the processor 10 starts an ultrasonic diagnosis (step S180). Note that the ultrasonic diagnosis continues until the end of the treatment. The continuation mentioned herein includes a case where the ultrasonic diagnosis is interrupted once for a predetermined reason and resumes afterwards. The predetermined reason mentioned herein is, for example, a case where the probe 150 in contact with the stomach wall or the like is away from the stomach wall or the like once to change the position of the probe 150 as described later. In step S180, specifically, the probe 150 is brought into contact with the stomach wall or the like in a state where the contracted stomach wall or the like is extended by supply of predetermined gas from an insufflation device, which is not illustrated, and ultrasonic waves are transmitted from the probe 150. With this operation, the probe 150 receives reflective waves of the ultrasonic waves, and the processor 10 generates the ultrasonic image based on the received signals. This enables acquisition of the ultrasonic image in the above-mentioned scan range. The predetermined gas is, for example, the air, but may be carbon dioxide. The air mentioned herein is gas having a component ratio that is equivalent to that of the atmospheric air. Since the carbon dioxide is quickly absorbed into the living body in comparison with the air, a burden on the subject after the manipulation can be reduced. The predetermined gas is, for example, supplied from an air supply nozzle in the distal end portion 130, but may be supplied from an air supply tube inserted into the above-mentioned overtube. The air supply nozzle is not illustrated.

Thereafter, the processor 10 controls the endoscope 100 in the second control mode AM2 (in step S200). Although details will be described later, the probe 150 is moved to a more accurate position based on the ultrasonic image acquired in the above-mentioned step S180. Note that step S200 can be omitted, and will be described in detail later.

Figure 7:
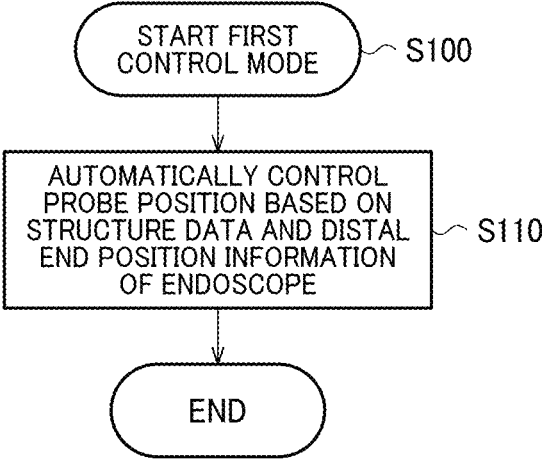
FIG. 7 is a flowchart describing a processing example in a first control mode.
Figure 8:
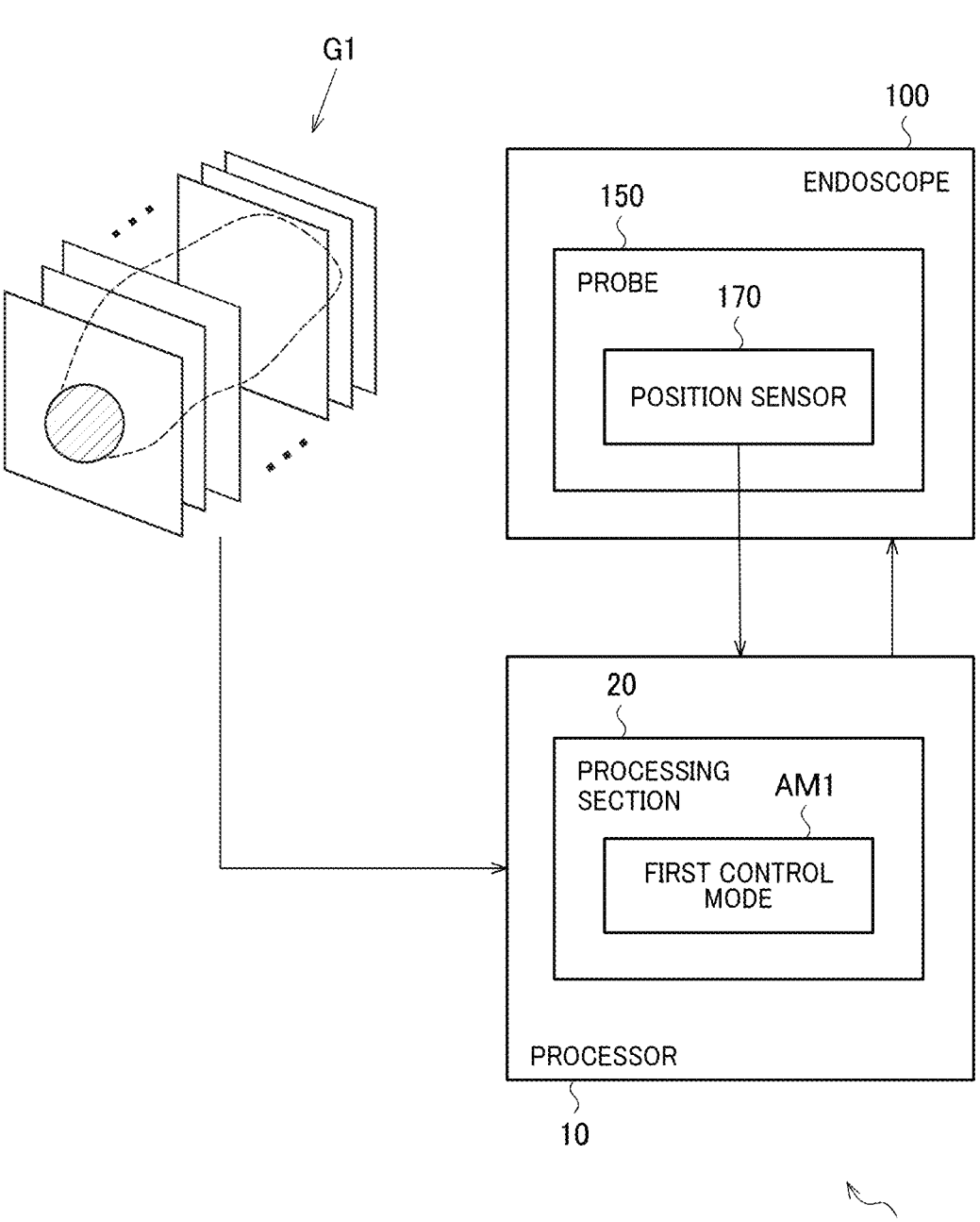
FIG. 8 is a diagram for describing an endoscope system that operates in the first control mode.

Step S100 in FIG. 6 is now described in more detail. In step S100 in FIG. 6, for example, a processing example shown in a flowchart of FIG. 7 is performed by the endoscope system 1 having a configuration example in FIG. 8. In FIG. 7, the processor 10 automatically controls the probe position based on the structure data and the distal end position information of the endoscope 100 (step S110). For example, as illustrated in FIG. 8, the processor 10 acquires the structure data indicated by G1 and the distal end position information of the endoscope 100 from a position sensor 170 included in the probe 150, and automatically controls the probe position based on these pieces of information. The position sensor 170 is, for example, arranged at a predetermined position of the distal end portion 130 as appropriate although not illustrated in detail. The position sensor 170 is implemented by, for example, a position detection device such as an inertial measurement unit (IMU). The IMU is an inertial sensor unit including a speed sensor and a gyro sensor. With this configuration, the processor 10 is capable of acquiring position information of the distal end portion 130 and six degrees of freedom (6DoF) information as direction information of the distal end portion 130 based on measurement data from the position sensor 170. Alternatively, the position sensor 170 may be implemented by, for example, a magnetic sensor. In addition, the position information can include the direction information.

The processor 10 collates the coordinate information set as the target position and the position information acquired by the position sensor 170 with each other, and thereby determines whether or not the probe 150 can be moved to the target position. Note that a model as indicated by D10 in FIG. 9 may be constructed using the structure data acquired in step S100, the position information acquired by the position sensor 170, or the like, and may be displayed as support presentation information on a predetermined display section. The predetermined display section mentioned herein is, for example, a display device 900 or the like. The display device 900 will be described later with reference to FIG. 11. With this configuration, for example, a three-dimensional model image including the lesion and indicated by D11 in FIG. 9 and a model image of the endoscope 100 that approaches the lesion as indicated by D12 are superimposed on each other, whereby guide display that assists the user in treatment can be performed. The model image of the endoscope 100 indicated by D12 is displayed so as to correspond to the position information acquired from the position sensor 170.

The processor 10 then performs the automatic control of the probe position until coordinates of the target position set in step S10 and the position information acquired by the position sensor 170 are matched with each other. For example, the processor 10 performs feedback control regarding advance/retreat of the insertion portion 110, which will be described later, and curving of the distal end portion 130.

Figure 10:
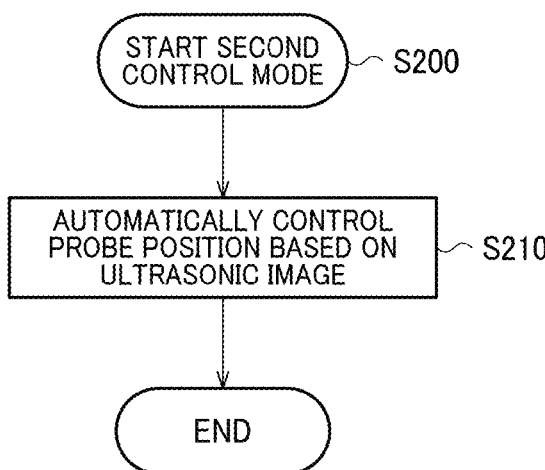
FIG. 10 is a flowchart for describing a processing example in a second control mode.

The second control mode AM2 is now described. In step S200 in FIG. 6, for example, the processor 10 automatically controls the probe position based on the ultrasonic image as described in the flowchart in FIG. 10 (step S210). Although not illustrated, for example, assume that the position of the lesion displayed in the ultrasonic image acquired in step S180 is not within the angle range indicated by R4 in FIG. 4. At this time, for example, the user calculates, from the ultrasonic image, an angle required to bring the lesion into the angle range indicated by R4 in FIG. 4, and performs programing to curve the curved portion 102 by the angle. The curved portion 102 will be described later. The processor 10 performs electric control to curve the curved portion 102 based on the program. That is, in step S210 mentioned herein, the processor 10 operates the endoscope 100 in the above-mentioned semi-automatic mode. This can create a state where the biopsy needle 410 is inserted into the lesion.

In this manner, the endoscope system 1 according to the present embodiment includes the processor 10 including hardware. The processor 10 acquires the structure data of the organ, acquires the endoscope image from the imager 180 of the endoscope 100, and acquires the ultrasonic image from the probe 150 of the endoscope 100. The processor 10 automatically controls the probe position of the endoscope 100 based on the structure data and distal end position information of the endoscope 100 in the first control mode AM1, and automatically controls the probe position based on the ultrasonic image in the second control mode AM2. In this manner, the endoscope system 1 according to the present embodiment includes the processor 10, and can thereby operate the endoscope 100 in the first control mode AM1 or the second control mode AM2. In the first control mode AM1, the processor 10 acquires the position of the probe 150 based on the structure data of the organ and the distal end position information of the endoscope 100, and can thereby automatically control the endoscope 100 so as to bring the probe 150 close to a desired position in various manipulations. In the second control mode AM2, the processor 10 automatically controls the position of the probe 150 based on the ultrasonic image that indicates the position of the lesion with higher accuracy, and can thereby arrange the probe 150 at a more desired position with higher accuracy. The endoscope system 1 that automatic controls the probe position using the first control mode AM1 and the second control mode AM2 like the present embodiment has never been proposed before.

The method according to the present embodiment may be implemented as a control method for acquiring the structure data of the organ, acquiring the endoscope image from the imager 180 of the endoscope 100, acquiring the ultrasonic image from the probe 150 of the endoscope 100, automatically controlling the probe position of the endoscope 100 based on the structure data and the distal end position information of the endoscope 100 in the first control mode AM1, and automatically controlling the probe position based on the ultrasonic image in the second control mode AM2. This enables obtaining of an effect that is similar to the above-mentioned effect.

The processor 10 in the endoscope system 1 according to the present embodiment may control the probe position in the first control mode AM1, and thereafter control the probe position in the second control mode AM2. This enables switching of an operation mode for automatically controlling the probe position in an appropriate order.

The method according to the present embodiment is applied to the motorized endoscope system 1 as described above. FIG. 11 illustrates a configuration example of the motorized endoscope system 1. The endoscope system 1 is a system for performing observation or treatment on the inside of the body of the subject lying on an operating table T. The endoscope system 1 includes the endoscope 100, a control device 600, the operation device 300, an advance/retreat drive device 800, and a treatment tool advance/retreat drive device 460, and the display device 900. The control device 600 includes a drive control device 200, and a video control device 500.

The endoscope 100 includes the above-mentioned insertion portion 110, a coupling element 125, an extracorporeal flexible portion 145, and connectors 201 and 202. The insertion portion 110, the coupling element 125, the extracorporeal flexible portion 145, and the connectors 201 and 202 are connected to one another in this order from the distal end side.

The insertion portion 110 is a portion inserted into a lumen of the subject, and is configured to be flexible and have a long and thin shape. The insertion portion 110 illustrated in FIG. 11 includes the curved portion 102, an intracorporeal flexible portion 119 that connects a base end of the curved portion 102 and the coupling element 125 to each other, and the distal end portion 130 arranged at the distal end of the curved portion 102. An internal path 101 is arranged inside the insertion portion 110, the coupling element 125, and the extracorporeal flexible portion 145, and a curved wire 160 passes through the internal path 101 and is connected to the curved portion 102. The curved wire 160 will be described later. The drive control device 200 drives the curved wire 160 via the connector 201 to perform a curving operation of the curved portion 102. The raising base operation wire 136, which has been described above with reference to FIG. 3, passes through the internal path 101 and is connected to the connector 201. That is, the drive control device 200 drives the raising base operation wire 136 to change the inclination angle of the raising base 135.

An image signal line that connects an imaging device included in the distal end portion 130 and the connector 202 passes through the internal path 101, and an image signal is transmitted from the imaging device to the video control device 500 via the image signal line. The imaging device is not illustrated. The video control device 500 displays an in-vivo image generated from the image signal on the display device 900. In addition, the ultrasonic cable 159 described above with reference to FIG. 3 passes through the internal path 101, and an echo signal is transmitted from the probe 150 to the video control device 500 via the ultrasonic cable 159. The video control device 500 functions as the above-mentioned ultrasonic observation device, and displays an ultrasonic image generated from the echo signal on the display device 900. Note that there may be a plurality of display devices 900, and the in-vivo image and the ultrasonic image may be displayed on the respective display devices 900.

In a case where various sensors including the angle sensor described above with reference to FIG. 3, the position sensor 170 described above with reference to FIG. 8, and the like are arranged in the distal end portion 130, various signal lines that connect the corresponding sensors and the connector 201 are arranged in the internal path 101, and various detection signals are transmitted from the various sensors to the drive control device 200 via the various signal lines.

The insertion opening 190 and a roll operation portion 121 are arranged in the coupling element 125. The roll operation portion 121 is attached to the coupling element 125 to be rotatable about an axis line direction of the insertion portion 110. The rotation operation of the roll operation portion 121 causes roll rotation of the insertion portion 110. As described later, the roll operation portion 121 can be electrically driven.

Figure 14:
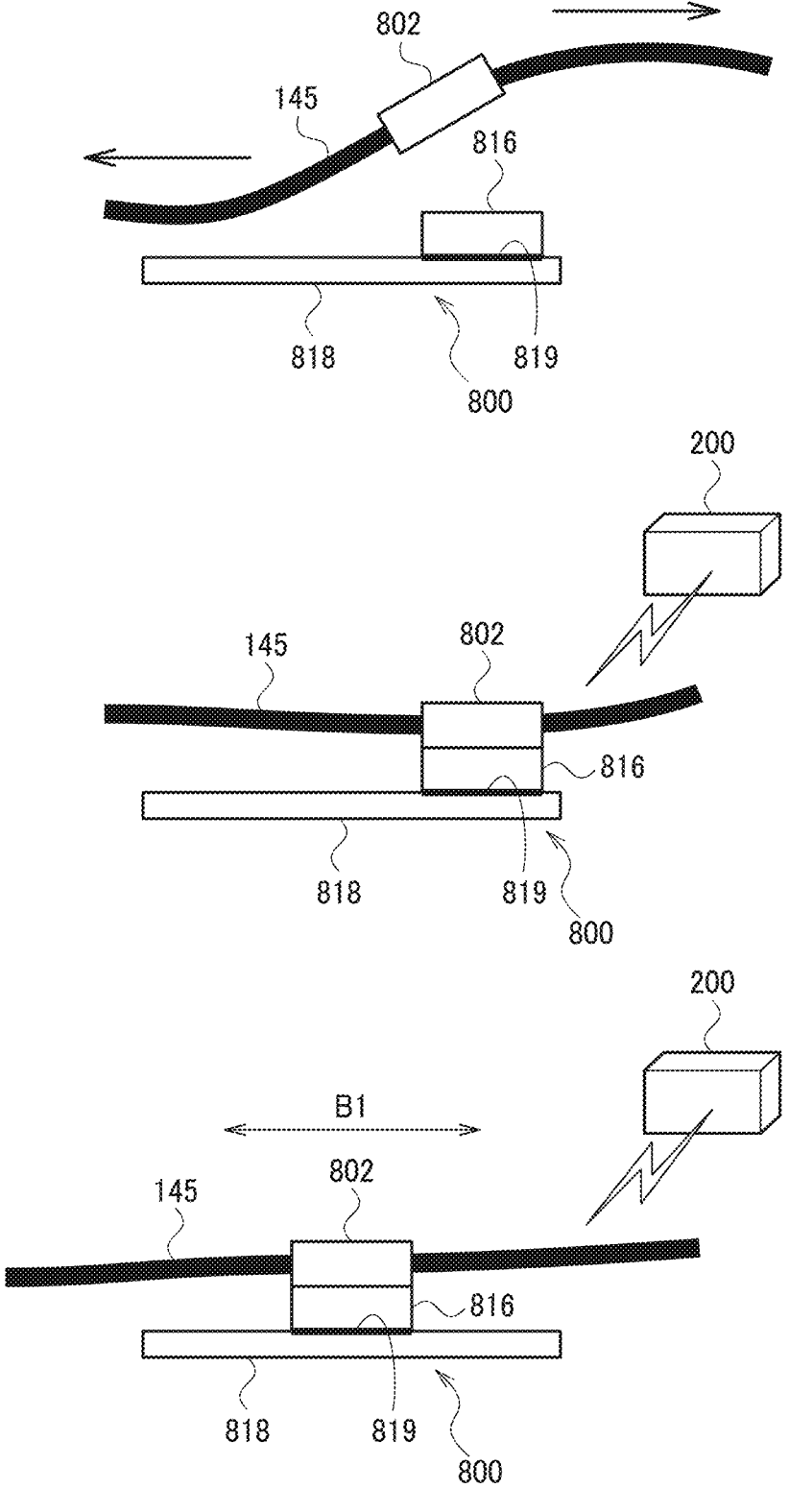
FIG. 14 is a diagram for describing a configuration example of an advance/retreat drive device.

The advance/retreat drive device 800 is a drive device that electrically drives the insertion portion 110 to advance/retreat the insertion portion 110, which will be described later in detail with reference to FIG. 14. The extracorporeal flexible portion 145 is attachable/detachable to/from the advance/retreat drive device 800, and the advance/retreat drive device 800 slides the extracorporeal flexible portion 145 in the axis line direction in a state where the extracorporeal flexible portion 145 is mounted on the advance/retreat drive device 800, whereby the insertion portion 110 advances/retreats. FIG. 14, which will be described later, illustrates an example in which the extracorporeal flexible portion 145 and the advance/retreat drive device 800 are attachable/detachable, but the configuration is not limited thereto, and the coupling element 125 and the advance/retreat drive device 800 may be configured to be attachable/detachable.

The treatment tool advance/retreat drive device 460 is a drive device that electrically drives the treatment tool 400 such as the biopsy needle 410 to advance/retreat, and has, for example, a configuration similar to that of the above-mentioned advance/retreat drive device 800. That is, for example, the sheath portion 411 of the biopsy needle 410 is attachable/detachable to/from the treatment tool advance/retreat drive device 460, and the treatment tool advance/retreat drive device 460 slides the sheath portion 411 in the axis line direction in a state where the sheath portion 411 is mounted on the treatment tool advance/retreat drive device 460, whereby the sheath portion 411 advances/retreats.

The operation device 300 is detachably connected to the drive control device 200 via an operation cable 301. The operation device 300 may perform wireless communication with the drive control device 200 instead of wired communication. When the user operates the operation device 300, a signal of the operation input is transmitted to the drive control device 200 via the operation cable 301, and the drive control device 200 electrically drives the endoscope 100 so as to perform an operation according to the operation input based on the signal of the operation input. The operation device 300 includes operation input sections that correspond to advance/retreat of the endoscope 100, a curving operation and roll rotation in two directions, an operation of the raising base 135, and the like. In a case where there is a non-motorized operation among these operations, an operation input section for the operation may be omitted.

The drive control device 200 drives an actuator such as a built-in motor based on an operation input to the operation device 300 to electrically drive the endoscope 100. Alternatively, in a case where the actuator is an external actuator outside the drive control device 200, the drive control device 200 transmits a control signal to the external actuator based on the operation input to the operation device 300 and controls electric driving. In addition, the drive control device 200 may drive a built-in pump or the like based on the operation input to the operation device 300 and cause the endoscope 100 to perform air supply/aspiration. The air supply/aspiration is performed via an air supply/aspiration tube that passes through the internal path 101. One end of the air supply/aspiration tube opens at the distal end portion 130 of the endoscope 100, and the other end thereof is connected to the drive control device 200 via the connector 201.

Figure 12:
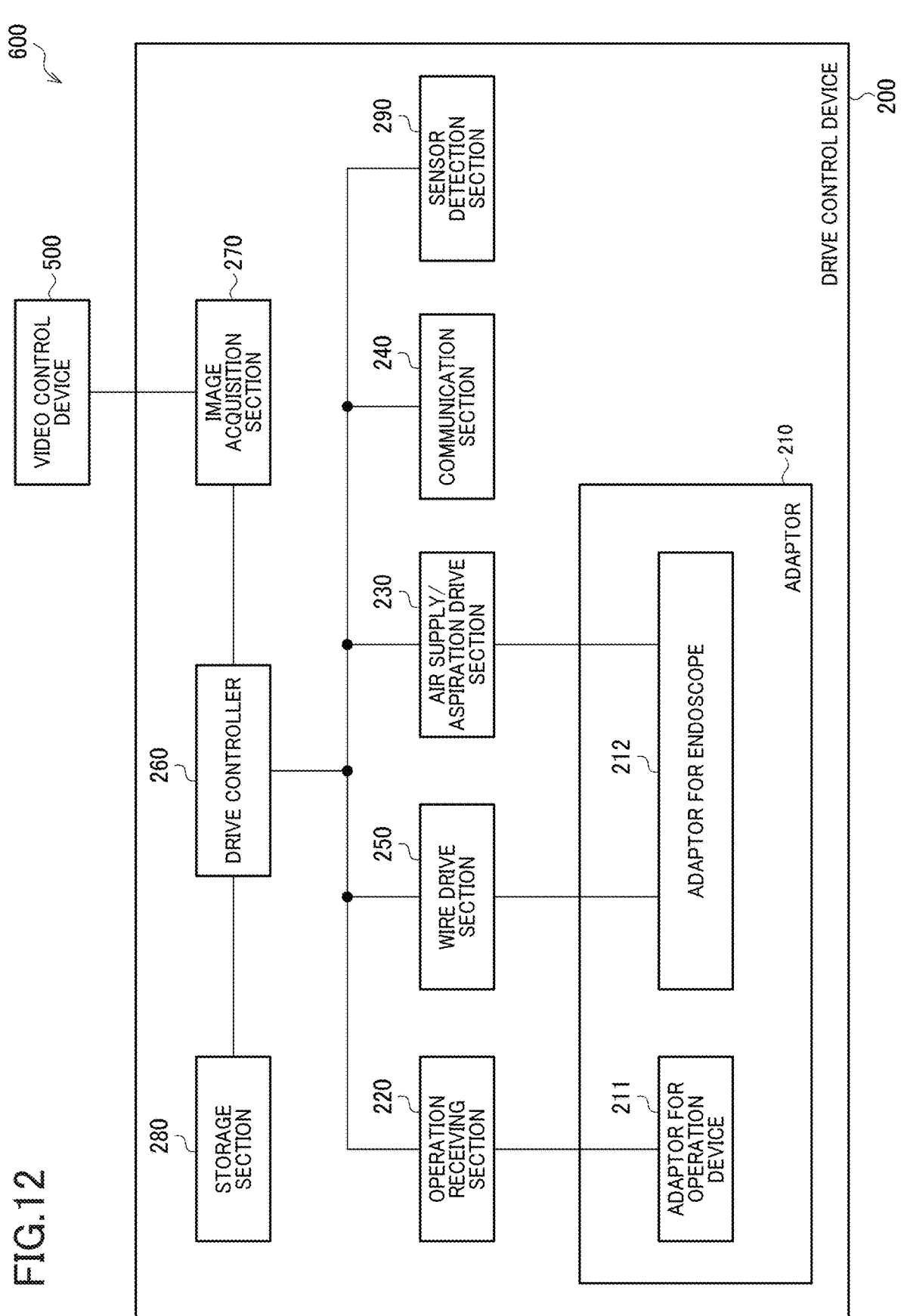
FIG. 12 is a diagram for describing a configuration example of a drive control device.

FIG. 12 illustrates a detailed configuration example of the drive control device 200. The drive control device 200 includes an adaptor 210, an operation receiving section 220, an air supply/aspiration drive section 230, a communication section 240, a wire drive section 250, a drive controller 260, an image acquisition section 270, a storage section 280, and a sensor detection section 290.

The adaptor 210 includes an adaptor for the operation device 211 to which the operation cable 301 is detachably connected and an adaptor for the endoscope 212 to which the connector 201 of the endoscope 100 is detachably connected.

The wire drive section 250 performs driving for the curving operation of the curved portion 102 of the endoscope 100 or the operation of the raising base 135, based on a control signal from the drive controller 260. The wire drive section 250 includes a motor unit for a curving operation to drive the curved portion 102 of the endoscope 100 and a motor unit for the raising base to drive the raising base 135. The adaptor for the endoscope 212 has a coupling mechanism for the curving operation for coupling to the curved wire 160 on the endoscope 100 side. The motor unit for the curving operation drives the coupling mechanism, whereby the driving force is transmitted to the curved wire 160 on the endoscope 100 side. The adaptor for the endoscope 212 has a coupling mechanism for the raising base for coupling to the raising base operation wire 136 on the endoscope 100 side. The motor unit for the raising base drives the coupling mechanism, whereby the driving force is transmitted to the raising base operation wire 136 on the endoscope 100 side.

The air supply/aspiration drive section 230 performs driving for air supply/aspiration of the endoscope 100 based on a control signal from the drive controller 260. The air supply/aspiration drive section 230 is connected to the air supply/aspiration tube of the endoscope 100 via the adaptor for the endoscope 212. The air supply/aspiration drive section 230 includes an insufflation device or the like, supplies the air to the air supply/aspiration tube, and sucks the air from the air supply/aspiration tube.

The communication section 240 performs communication with an external drive device arranged outside the drive control device 200. Communication may be either wireless communication or wired communication. The external drive device is the advance/retreat drive device 800 that performs advance/retreat, a roll drive device 850 that performs roll rotation, or the like. The roll drive device 850 will be described later with reference to FIG. 15.

The drive controller 260 controls the advance/retreat of the endoscope 100, the curving operation and the roll rotation, the inclination angle of the biopsy needle 410 formed by the raising base 135, and the air supply/aspiration by the endoscope 100. The drive controller 260 is hardware corresponding to the processor 10 illustrated in FIG. 1 or the like.

The drive controller 260 controls electric driving based on a signal of an operation input from the operation receiving section 220. Specifically, when the curving operation of the curved portion 102 is performed, the drive controller 260 outputs a control signal indicating a curving direction or a curving angle to the wire drive section 250, and the wire drive section 250 drives the curved wire 160 so that the curved portion 102 is curved in the curving direction or at the curving angle. When advance/retreat is performed, the drive controller 260 transmits a control signal indicating an advance/retreat direction or an advance/retreat movement amount to the advance/retreat drive device 800 via the communication section 240, and the advance/retreat drive device 800 advances/retreats the extracorporeal flexible portion 145 so that the endoscope 100 advances/retreats in the advance/retreat direction or the advance/retreat movement amount. When the roll rotation operation is performed, the drive controller 260 transmits a control signal indicating a roll rotation direction or a roll rotation angle to the roll drive device 850, which will be described later, via the communication section 240, and the roll drive device 850 roll rotates the insertion portion 110 in the roll rotation direction or at the roll rotation angle. Similar control is performed for another electric driving.

The sensor detection section 290 detects an output signal from, for example, the above-mentioned various sensors such as the position sensor 170 and the angle sensor. The sensor detection section 290 includes, for example, an amplification circuit that amplifies output signals from the various sensors or the like, and an analog/digital (A/D) converter that performs A/D conversion on an output signal from the amplification circuit and outputs detection data to the drive controller 260. The drive controller 260 performs control of the position of the probe 150, control of the inclination angle of the raising base 135, or the like, based on the detection data.

In addition, the drive controller 260 controls the above-mentioned biopsy needle 410 based on the ultrasonic image acquired from the image acquisition section 270 and the signal of the operation input from the operation receiving section 220. In a case of using machine learning, the trained model 22 is stored in the storage section 280. The machine learning and the trained model 22 will be described later. That is, the storage section 280 in FIG. 12 corresponds to the memory 12 in FIG. 17.

Figure 13:
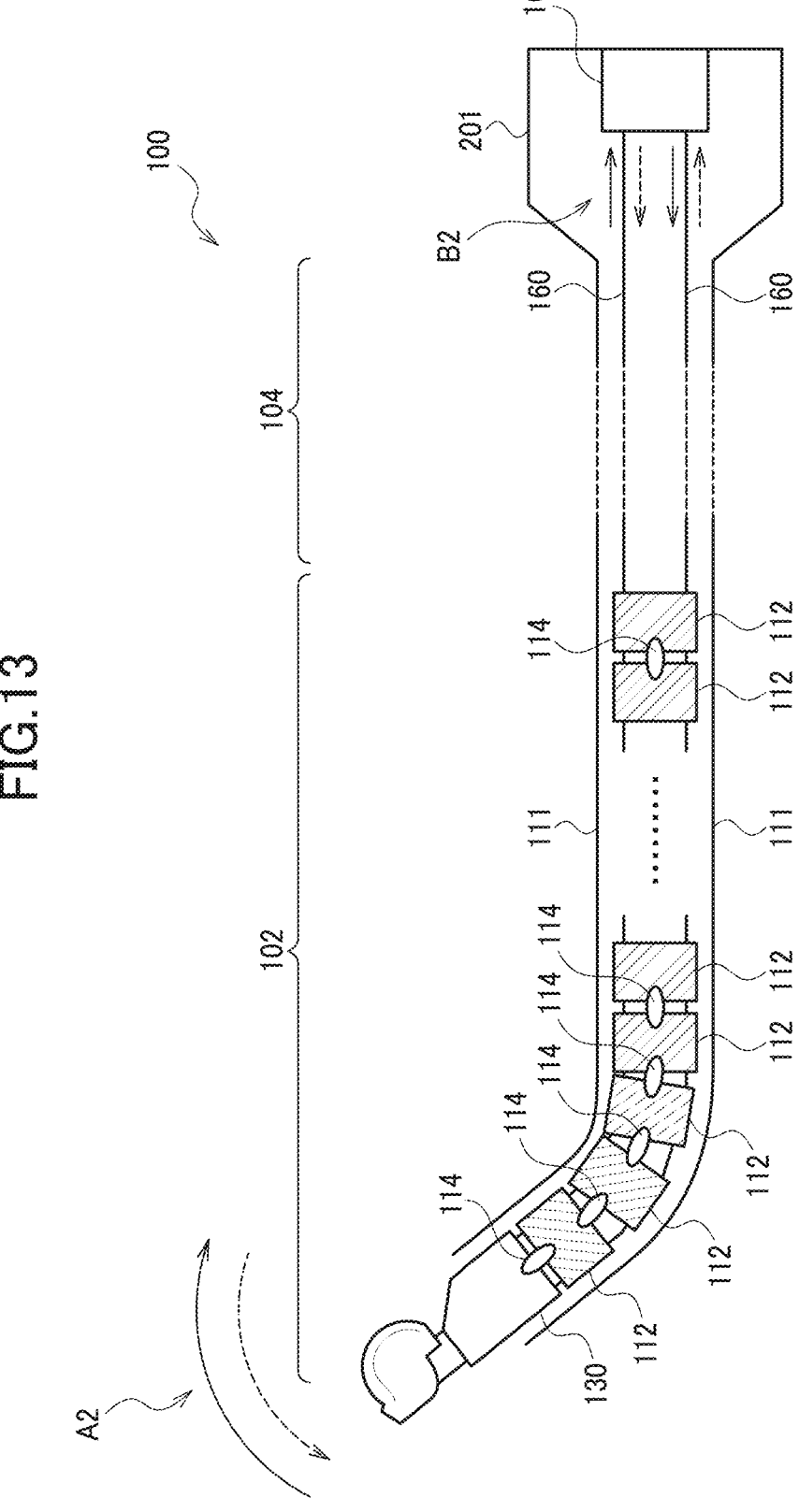
FIG. 13 is a diagram for describing a curved portion and a drive mechanism for the curved portion.

FIG. 13 is a diagram schematically illustrating the endoscope 100 including the curved portion 102 and a drive mechanism for the curved portion 102. The endoscope 100 includes the above-mentioned curved portion 102, a flexible portion 104, and the connector 201. Note that the flexible portion 104 corresponds to the above-mentioned intracorporeal flexible portion 119 and the extracorporeal flexible portion 145, and the coupling element 125 is not illustrated in FIG. 13.

The curved portion 102 and the flexible portion 104 are covered with an outer sheath 111. The inside of the tube of the outer sheath 111 corresponds to the internal path 101 in FIG. 11. The curved portion 102 includes a plurality of curving pieces 112 and the distal end portion 130 that is coupled to a distal end of the curving pieces 112. The plurality of curving pieces 112 and the distal end portion 130 are connected by corresponding pivotable coupling elements 114 in series from the base end side to the distal end side, and have a multiple joint structure. A coupling mechanism 162 on the endoscope side is arranged in the connector 201. The coupling mechanism 162 is connected to a coupling mechanism on the drive control device 200 side. The connector 201 is mounted on the drive control device 200, whereby it becomes possible to perform electric driving for the curving operation. The curved wire 160 is arranged inside the outer sheath 111. One end of the curved wire 160 is connected to the distal end portion 130. The curved wire 160 penetrates the plurality of curving pieces 112, passes the flexible portion 104, folds back inside the coupling mechanism 162, passes the flexible portion 104 again, and penetrates the plurality of curving pieces 112. The other end of the curved wire 160 is connected to the distal end portion 130. Driving force from the wire drive section 250 is transmitted as tractive force to the curved wire 160 via the coupling mechanism 162.

As indicated by an arrow of a solid line in B2, when a wire on an upper side of the drawing is pulled, a wire on a lower side of the drawing is pushed, whereby a multiple joint of the curving pieces 112 is bent in an upper direction of the drawing. With this operation, as indicated by an arrow of a solid line in A2, the curved portion 102 is curved in the upper direction of the drawing. In a case where the wire on the lower side of the drawing is pulled as indicated by an arrow by a dotted line in B2, the curved portion 102 is similarly curved in a lower direction of the drawing as indicated by a dotted line in A2. Note that the curved portion 102 is capable of being curved independently in two directions that are orthogonal to each other. FIG. 13 illustrates a curving mechanism only for one direction, but two sets of curved wires 160 are actually arranged. Each curved wire 160 is pulled independently by the coupling mechanism 162, and can thereby be curved independently in two directions.

Note that a mechanism for electrical driving for curving is not limited to the above-mentioned mechanism. For example, a motor unit may be arranged in substitution for the coupling mechanism 162. Specifically, the drive control device 200 transmits a control signal to the motor unit via the connector 201 and the motor unit may perform driving for the curving operation by pulling or loosening the curved wire 160 based on the control signal.

FIG. 14 illustrates a configuration example of the advance/retreat drive device 800. The advance/retreat drive device 800 includes a motor unit 816, a base 818, and a slider 819. As illustrated in an upper drawing and a middle drawing, the extracorporeal flexible portion 145 of the endoscope 100 is provided with an attachment 802 that is detachably mounted on the motor unit 816. As illustrated in the middle drawing, the attachment 802 is mounted on the motor unit 816, whereby it becomes possible to perform electric driving for advance/retreat. As illustrated in a lower drawing, the slider 819 supports the motor unit 816 so as to be linearly movable with respect to the base 818. The slider 819 is fixed to the operating table T illustrated in FIG. 11. As indicated by B1, the drive control device 200 transmits a control signal for advance/retreat to the motor unit 816 through wireless communication, and the motor unit 816 and the attachment 802 linearly move over the slider 819 based on the control signal. With this operation, advance/retreat of the insertion portion 110 can be implemented. Note that the drive control device 200 and the motor unit 816 may have a wired connection.

Although not illustrated, the treatment tool advance/retreat drive device 460 may also be configured to include a motor unit, a base, and a slider. In addition, an attachment detachably mounted on the motor unit may be arranged in the sheath portion 411 of the biopsy needle 410. Although not illustrated, each of the needle and stylet of the needle portion 412 included in the biopsy needle 410 may be electrically controlled. For example, each of the needle and the stylet described above is connected to a motorized cylinder. The drive control device 200 then transmits a predetermined control signal to the motorized cylinder, and the needle and the stylet operate based on the control signal. Either the needle or the stylet may be electrically controlled.

Figure 15:
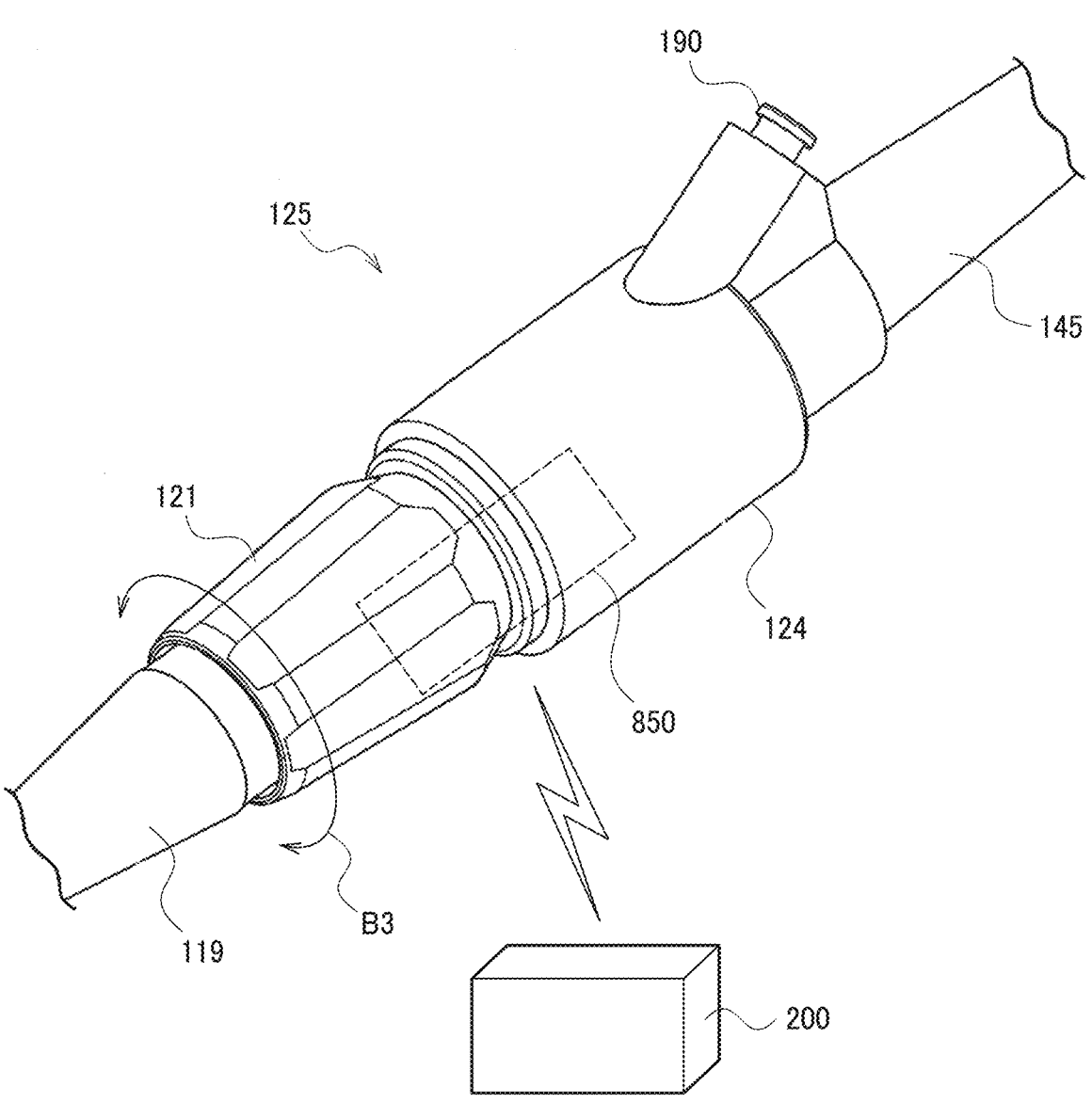
FIG. 15 is a diagram for describing a configuration example of a coupling element including a roll drive device.

FIG. 15 is a perspective view illustrating the coupling element 125 including the roll drive device 850. The coupling element 125 includes a coupling element main body 124 and the roll drive device 850.

The insertion opening 190 is arranged in the coupling element main body 124, and is connected to the treatment tool insertion path, which is not illustrated in FIG. 15, inside the coupling element main body 124. The coupling element main body 124 has a cylindrical shape, and a cylindrical member that is coaxial with a cylinder of the coupling element main body 124 is rotatably arranged inside the coupling element main body 124. A base end portion of the intracorporeal flexible portion 119 is fixed to the outside of the cylindrical member, and the base end portion serves as the roll operation portion 121. This allows the intracorporeal flexible portion 119 and the cylindrical member are rotatable with respect to the coupling element main body 124 about the axis line direction of the intracorporeal flexible portion 119. The roll drive device 850 is the motor unit arranged inside the coupling element main body 124. As indicated by B3, the drive control device 200 transmits a control signal for roll rotation to the roll drive device 850 through wireless communication, and the roll drive device 850 rotates the base end portion of the intracorporeal flexible portion 119 with respect to the coupling element main body 124 based on the control signal, whereby the intracorporeal flexible portion 119 roll rotates. Note that the roll drive device 850 may include a clutch mechanism, which switches between non-electric driving and electric driving of the roll rotation. Note that the drive control device 200 and the roll drive device 850 may have a wired connection using a signal line that passes the internal path 101.

Figure 16:
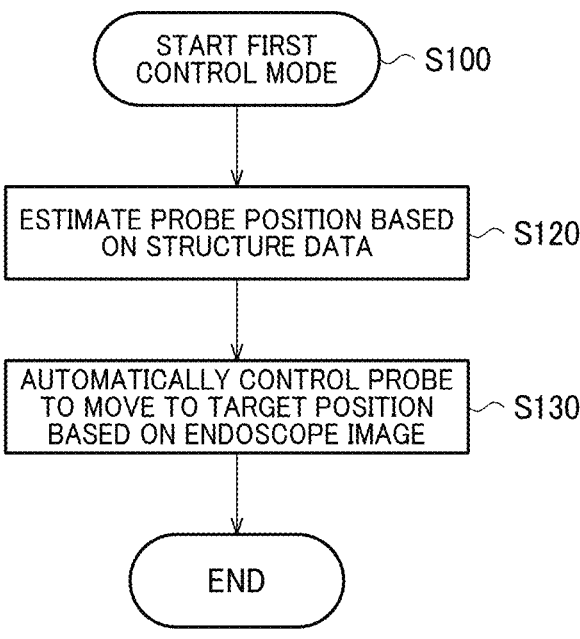
FIG. 16 is a flowchart for describing another processing example in the first control mode.

The method according to the present embodiment is not limited to the above-mentioned method, and can be modified in various manners. For example, step S100 may be implemented like a processing example described in FIG. 16. The processor 10 estimates the target position of the probe 150 based on the structure data (step S120), and thereafter automatically controls the probe 150 to move to the target position based on the endoscope image (step S130). In step S120, for example, the processor 10 sets the target position based on the three-dimensional shape information that is reconstructed in step S10 as described above.

Step S130 includes processing of measuring a three-dimensional shape of a lumen faced by the objective lens 132 based on, for example, the captured endoscope image, and generating a three-dimensional image. Step S130 further includes processing of collating the generated three-dimensional image and a three-dimensional image according to the structure data acquired in step S10 with each other, and thereby identifying the position of the three-dimensional image generated in step S130. Step S130 further includes processing of calculating position information indicating the probe position from the identified position of the three-dimensional image. For example, the processor 10 calculates the position information of the objective lens 132 based on the identified position of the three-dimensional image, and calculates the position information of the probe position based on the calculated position information of the objective lens 132. With this processing, the processor 10 compares the position information of the target position estimated in step S120 and the position information of the probe position calculated in step S130, and can thereby determine whether the probe position approaches the probe position. Although not described as the flowchart, when determining that a difference between the positional information of the probe position calculated in step S130 and the position information of the target position estimated in step S120 is within a predetermined range, the processor 10 ends step S100.

As a method of measuring the three-dimensional shape regarding the lumen based on the endoscope image, for example, a pattern light projection method can be used. Specifically, for example, the processing section 20 includes a program that emits predetermined pattern light to a light emission device, which is not illustrated. The processor 10 reads out and executes the program to project predetermined pattern light onto the lumen via the illumination lens 133. As the predetermined pattern light, multitude kinds of known pattern light such as grating pattern light and stripe pattern light have been proposed, any predetermined pattern light can be adopted. The processor 10 uses the endoscope image of the lumen captured by irradiation of uniform illumination light, the endoscope image of the lumen captured by irradiation of the predetermined pattern light, optical information of the imager 180, or the like to calculate depth information at each position of the captured image of the lumen based on the triangulation principle. Thereafter, the processor 10 generates the three-dimensional image based on the endoscope image captured by irradiation of the uniform illumination light and the calculated depth information.

Note that the processing of measuring the three-dimensional shape is not limited to the above-mentioned pattern light projection method, another light projection method such as a spot light projection method and a slit light projection method, or a passive stereo method or the like may be used, or each section of the imager 180 may be configured so that any one of these methods is applied thereto. Since these methods are known well, detailed description thereof is omitted. In a case where the distal end position information of the endoscope 100 is obtained by the method of measuring the three-dimensional shape in this manner, the position sensor 170 is not necessarily used in step S100. In this case, the position sensor 170 may be used in the second control mode AM2, which will be described later. Therefore, in the first control mode AM1, the processor 10 in the endoscope system 1 according to the present embodiment obtains the distal end position information based on the endoscope image, and automatically controls the probe position based on the obtained distal end position information and the obtained structure data (step S130). As a result, it becomes possible to construct the endoscope system 1 that automatically controls the position of the probe 150 based on the structure data and the captured endoscope image.

In the first control mode AM1, the processor 10 in the endoscope system 1 of the present embodiment may estimate the target position of the probe 150 based on the structure data (step S120), and automatically control the probe position to the estimated target position based on the endoscope image (step S130). With this processing, the processor 10 is capable of automatically controlling the probe 150 so as to approach the preliminarily estimated target position.

Figure 17:
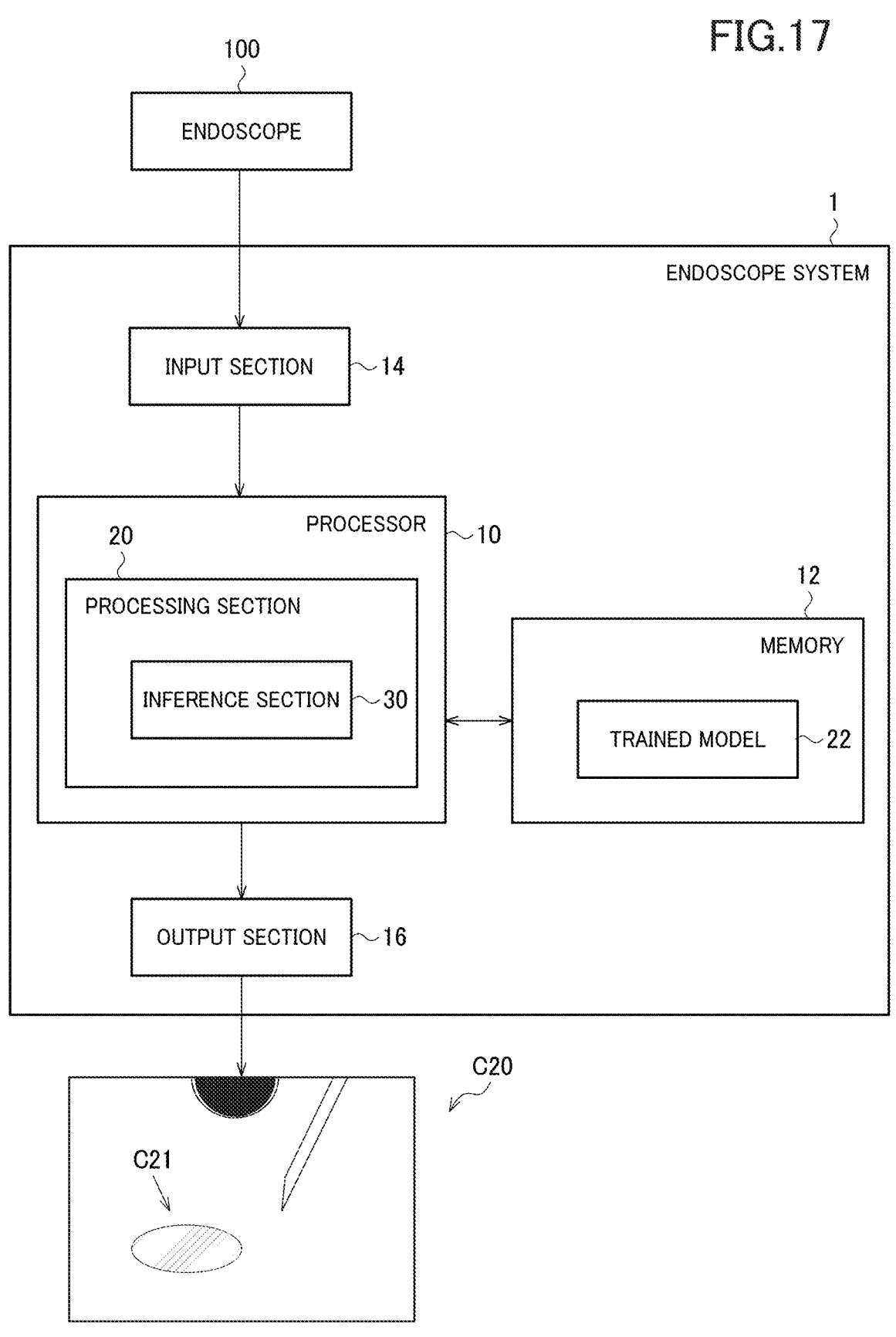
FIG. 17 is a diagram for describing another configuration example of the endoscope system.

In addition, the endoscope system 1 of the present embodiment may detect a region regarding the lesion as the region marker information from the ultrasonic image acquired from the endoscope 100 and display the region marker information so as to be superimposed on the ultrasonic image. Specifically, for example, the endoscope system 1 of the present embodiment is configured like a configuration example illustrated in FIG. 17, and can thereby implement detection of the region marker information. In FIG. 17, the endoscope system 1 includes, in addition to the processor 10 including the above-mentioned processing section 20, the memory 12 that stores the trained model 22, an input section 14, and an output section 16. In addition, the processing section 20 includes an inference section 30. Specifically, for example, the processing section 20 reads out the trained model 22 from the memory 12, executes the program regarding the trained model 22, and thereby functions as the inference section 30.

The input section 14 is an interface that receives input data from the outside. Specifically, the input section 14 is an image data interface that receives the ultrasonic image as a processing target image. For example, the input section 14 uses the received ultrasonic image as the input data to the trained model 22 and the inference section 30 performs inference, whereby a function as the input section 14 is implemented.

The output section 16 is an interface that transmits data estimated by the inference section 30 to the outside. For example, the output section 16 outputs output data from the trained model 22 as an ultrasonic image indicated by C20 in FIG. 17, whereby a function as the output section 16 is implemented. The ultrasonic image indicated by C20 is displayed so that region marker information indicated by C21 is superimposed thereon. That is, when the endoscope 100 captures the ultrasonic image, the region marker information indicated by C21 is automatically displayed. An output destination of the output data is, for example, the display device 900 as the above-mentioned predetermined display section. For example, the output section 16 serves as an interface that can be connected to the display device 900, whereby an image that is obtained by superimposing the ultrasonic image and the region marker information on each other is displayed on the display device 900, whereby a function as the output section 16 is implemented.

As an acquisition method for acquiring the region marker information, it is possible to use a method of segmenting the ultrasonic image into a plurality of regions by semantic segmentation and using a region from which the lesion can be read based on a result of segmentation as the region marker information, or another method.

In the trained model 22 of the present embodiment, a neural network, which is not illustrated, is included in at least part of the model. Models of various kinds of configurations are known as the neural network. In the present embodiment, for example, a convolutional neural network (CNN) can be applied as a model that implements the above-mentioned semantic segmentation. With use of the trained model 22 including the CNN or the like, the ultrasonic image indicated by C20 is eventually output. A region indicated by C21 is detected by segmentation in the ultrasonic image indicated by C20, and is displayed as the region marker information so as to be superimposed on the ultrasonic image. For example, the user can easily grasp that the lesion in the structure data indicated by D11 in FIG. 9 corresponds to the segmented region indicated by C21 in FIG. 17 in the ultrasonic image. A target of segmentation is not limited to the lesion, and may be, for example, an important tissue. The important tissue mentioned herein is a tissue that the biopsy needle 410 should be avoided from coming in contact with, for example, an organ such as the liver, the kidney, the pancreas, the spleen, and the gallbladder, and blood vessels, and is considered to be in a normal state in appearance.

In this manner, the endoscope system 1 of the present embodiment includes the memory 12 that stores the trained model 22 trained to output the region marker information as a detection target in the ultrasonic image. In the second control mode AM2, the processor 10 in the endoscope system 1 of the present embodiment detects at least one of the region marker information of the lesion or the region marker information of the important tissue based on the ultrasonic image and the trained model 22. With this configuration, the processor 10 is capable of automatically performing display so that the region marker information is superimposed on the ultrasonic image captured by the endoscope 100.

The processing regarding the second control mode AM2 may be executed in a modified manner as described below.

Figure 18:
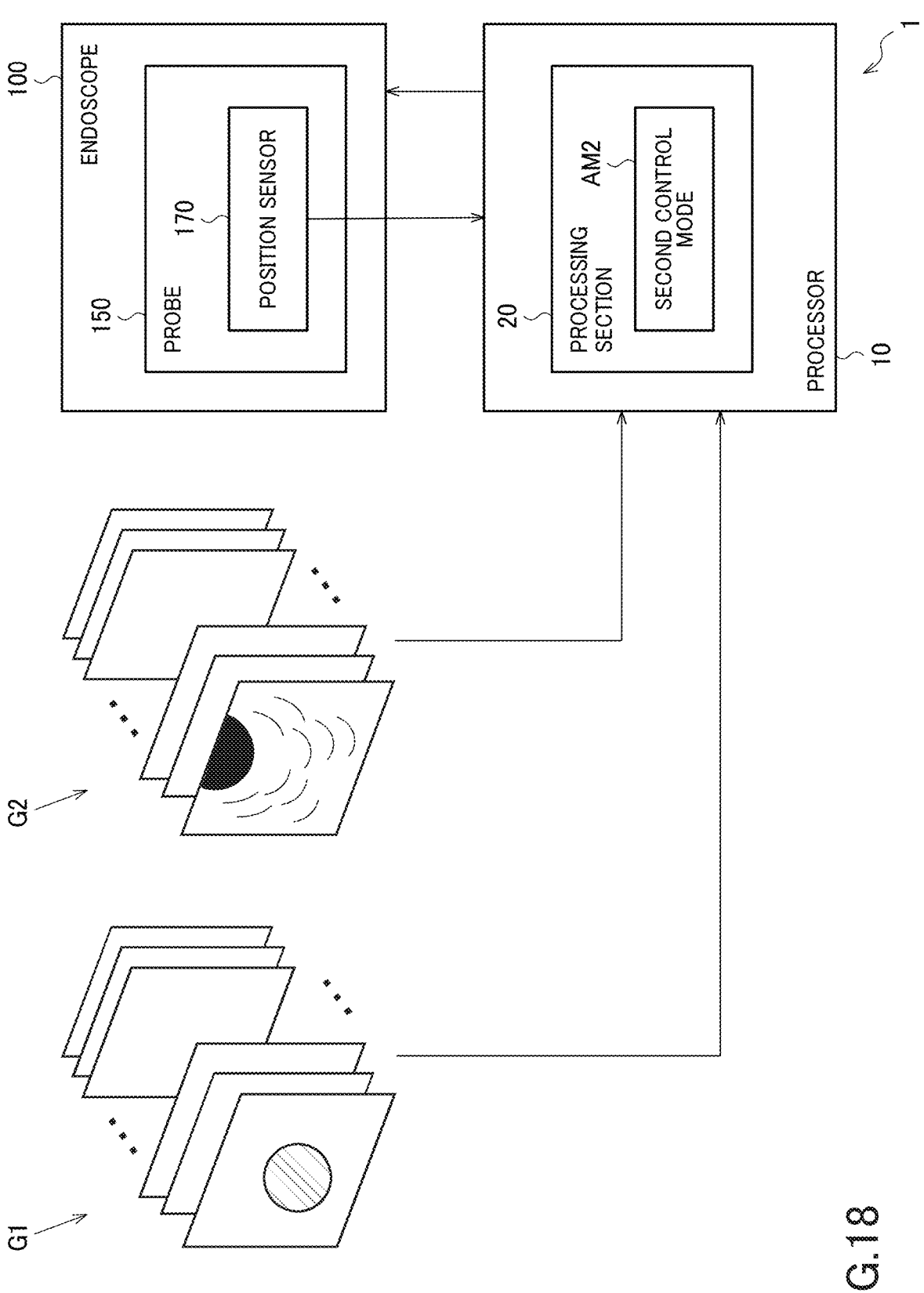
FIG. 18 is a diagram for describing the endoscope system that operates in the second control mode.
Figure 19:
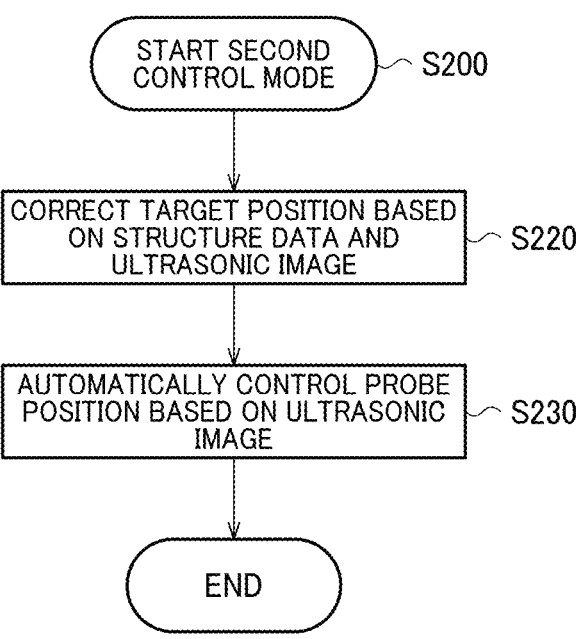
FIG. 19 is a flowchart for describing another processing example in the second control mode.

Specifically, processing described in a flowchart in FIG. 19 may be executed by the endoscope system 1 indicated as a configuration example in FIG. 18. In FIG. 19, for example, the processor 10 corrects the target position based on the structure data and the ultrasonic image (step S220), and thereafter automatically controls the probe position based on the ultrasonic image (in step S230).

For example, in step S180 in FIG. 6, the processor 10 moves the probe 150 in a state of being in contact with the stomach wall or the like in a certain range within the predetermined range including the target position estimated in step S100, and acquires the ultrasonic image. At this time, position information is attached to the ultrasonic image acquired by the position sensor 170 included in the probe 150. The processor 10 then performs volume rendering or the like on each of acquired ultrasonic images based on the position information, and thereby generates three-dimensional images based on the ultrasonic images. With this processing, the processor 10 is capable of acquiring the three-dimensional images based on the ultrasonic images as indicated by G2 in FIG. 18. A coordinate space in an ultrasonic image based on a three-dimensional image may be hereinafter referred to as a second coordinate space.

Figure 9:
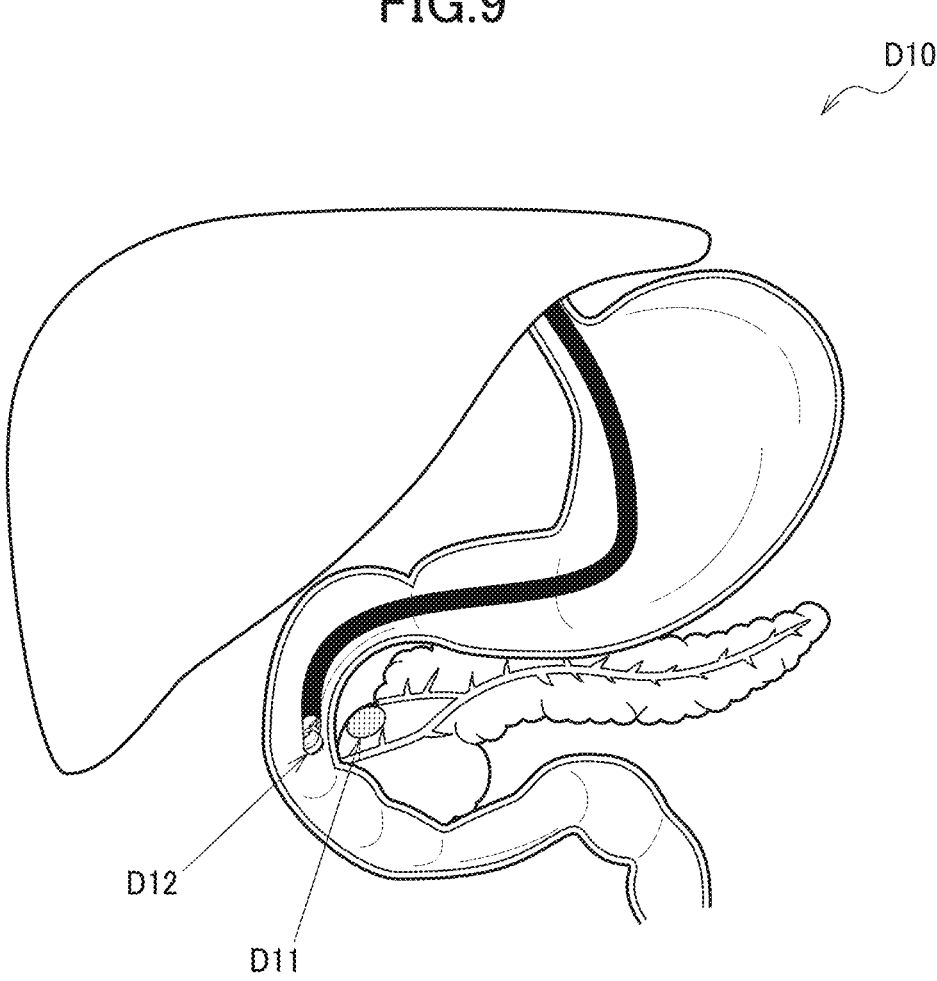
FIG. 9 is a diagram for describing an example of a guide display using structure data and distal end position information of an endoscope.

Step S220 includes processing of associating the above-mentioned first coordinate space and the second coordinate space with each other. The processor 10 also acquires the structure data indicated by G1 in FIG. 18 similarly to the case of FIG. 8. As described above, the lesion as the treatment target as indicated by D11 in FIG. 9 is identified in the structure data, and the lesion as the treatment target as indicated by C21 in FIG. 17 is identified in the ultrasonic image. The processor 10 then performs processing of calculating coordinates of the lesion in the first coordinate space and coordinates of the lesion in the second coordinate space, and processing of converting the position information of the lesion in the first coordinate space into the position information of the lesion in the second coordinate space and calculating a difference therebetween.

In step S230, the processor 10 then performs processing of automatically controlling the position of the probe 150 based on the difference calculated in step S220. For example, the user performs programming so that the endoscope 100 advances/retreats, curves, or the like so as to correspond to the difference calculated in step S220. The processor 10 then electrically controls the endoscope 100 based on the program. In this manner, in the second control mode AM2, the processor 10 in the endoscope system 1 of the present embodiment automatically controls the probe position based on the structure data and the ultrasonic image. With this processing, the processor 10 is capable of arranging the probe 150 at a desired position with higher accuracy.

In the second control mode AM2, the processor 10 in the endoscope system 1 of the present embodiment may automatically control the probe position based on the position of the treatment target identified based on the ultrasonic image. With this processing, the position information of the ultrasonic image and the position information of the structure data can be associated with each other.

The processor 10 in the endoscope system 1 of the present embodiment may correct the probe position estimated in the first control mode AM1 based on the position of the treatment target. With this processing, it becomes possible to change the probe position information estimated from the structure data to more accurate position information.

Figure 20:
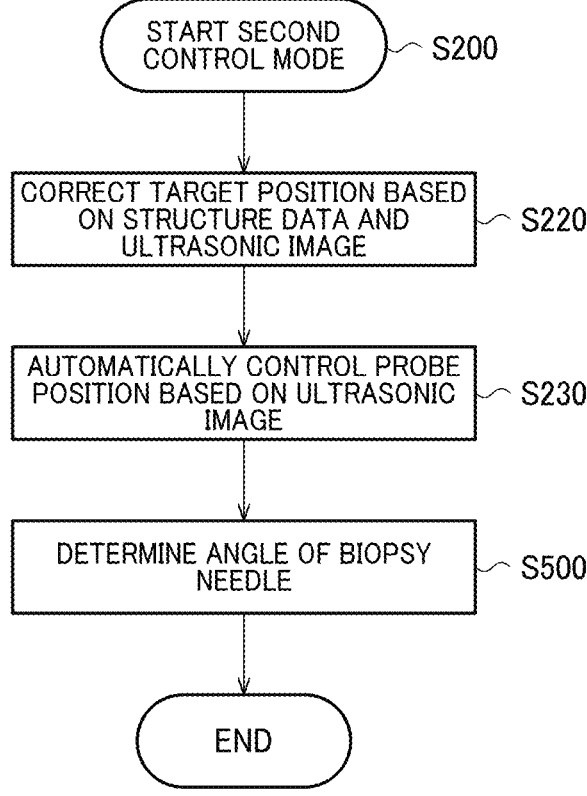
FIG. 20 is a flowchart for describing another processing example in the second control mode.

In addition, the processing regarding step S200 may be implemented as a processing example indicated by a flowchart in FIG. 20. The flowchart in FIG. 20 is different from the flowchart in FIG. 19 in that processing of determining the above-mentioned angle of the biopsy needle 410 (step S500) is added. As described above, the biopsy needle 410 is movable within the range indicated by R4 in FIG. 4. In step S500, the processor 10 detects the presence of the lesion within the movable range of the biopsy needle 410 by a method, which will be described later, and determines the angle of the biopsy needle 410 for insertion of the biopsy needle 410 into the lesion. That is, in the second control mode AM2, the processor 10 in the endoscope system 1 of the present embodiment calculates the angle of the biopsy needle 410 for insertion of the biopsy needle 410 into the lesion based on the movable range of the biopsy needle 410 (step S500). This allows the user to easily perform an operation of inserting the biopsy needle 410 while watching the ultrasonic image.

Figure 21:
FIG. 21 is a diagram for describing an example of a method of determining an angle of the biopsy needle.
Figure 21:
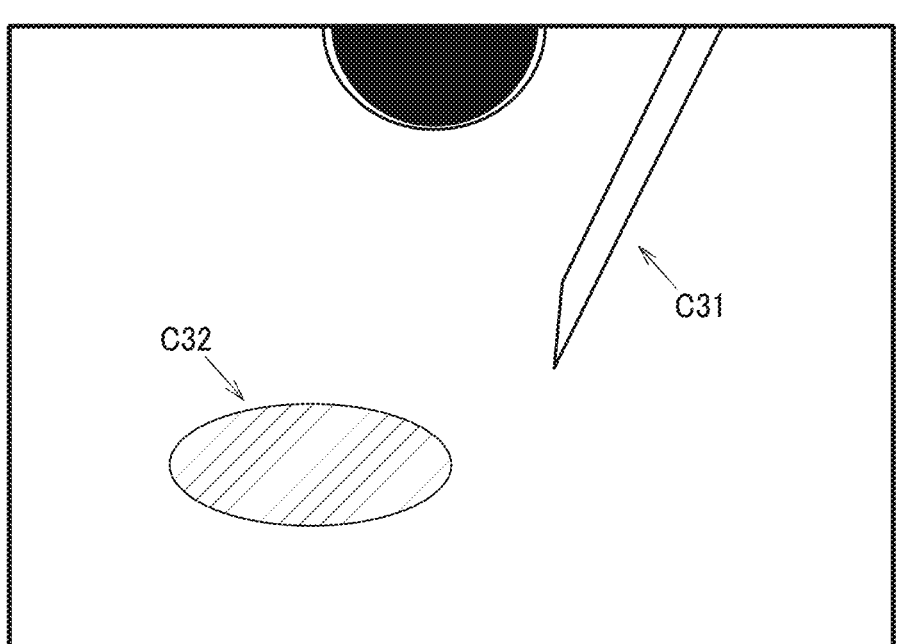
Figure 21:
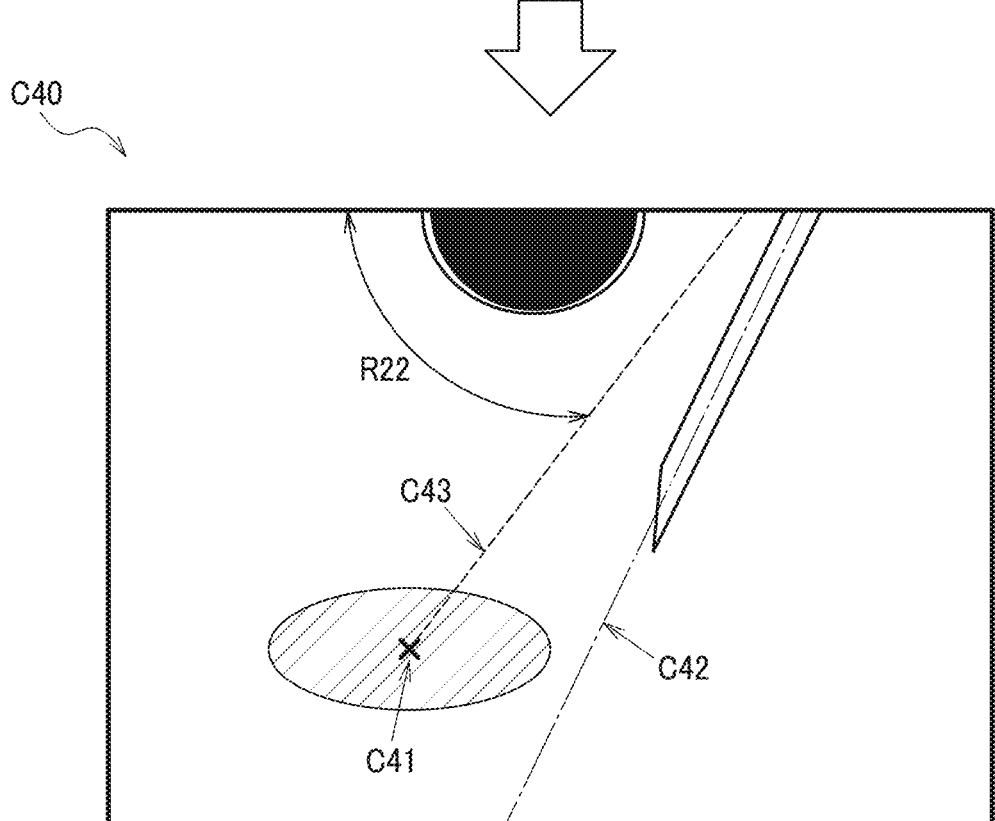

For example, in the ultrasonic image indicated by C30 in FIG. 21, assume that an image corresponding to the biopsy needle 410 indicated by C31 and region marker information of the lesion indicated by C32 are displayed. The region marker information of the lesion indicated by C32 is subjected to segmentation by the trained model 22 as described above, but may be a landmark added by the user using a drawing function of the touch panel, for example. Assume that the region marker information of the lesion indicated by C32 is within the movable range of the biopsy needle 410.

The processor 10 calculates a specific position for insertion of the biopsy needle 410 with respect to the region marker information of the lesion indicated by C32. The specific position is, for example, the centroid of the region marker information of the lesion, but may be the center, an outside edge, or the like, or a position instructed by the user with the touch panel or the like. Assume that the processor 10 calculates a position of a mark indicated by C41 as the specific position in an ultrasonic image indicated by C40.

The processor 10 then calculates the angle of the biopsy needle 410 for insertion of the biopsy needle 410 into the lesion. As described above, for example, since the movable range image is an image including regions predetermined by design, when the angle of the biopsy needle 410 is determined, an aggregation of coordinates included in the image of the biopsy needle 410 displayed on the ultrasonic image is unambiguously determined. Hence, for example, the endoscope system 1 performs processing of referring to a third table that associates the angle of the biopsy needle 410 and coordinates of the image of the biopsy needle 410 with each other and searching for the angle of the biopsy needle 410 corresponding to coordinates of the specific position. With this processing, for example, the processor 10 calculates a second straight line passing the specific position as indicated by C43 and the angle of the biopsy needle 410 as indicated by R22 based on the second straight line. For example, the processor 10 may display a first straight line indicated by C42 as an image, and display an instruction for matching the image of the first straight line with an image of the second straight line as operation support information, which will be described later.

As described above, in the second control mode AM2, the processor 10 in the endoscope system 1 of the present embodiment acquires an image in which the region marker information of the lesion is set, and calculates the angle of the biopsy needle 410 for insertion of the biopsy needle 410 into the lesion based on the movable range of the biopsy needle 410 and the region marker information. This allows the user to easily perform an operation of inserting the biopsy needle 410 into the lesion while watching the ultrasonic image.

As described above, the important tissue may be further segmented, and the angle of the biopsy needle 410 may be determined with use of region marker information of the lesion and region marker information of the important tissue. For example, although not illustrated, the user sets the specific position so that the above-mentioned second straight line passes the region marker information of the lesion and does not pass through the region marker information of the important tissue. The processor 10 then calculates the second straight line so as to pass the set specific position and the angle of the biopsy needle 410 based on the second straight line. In this manner, in the second control mode AM2, the processor 10 in the endoscope system 1 of the present embodiment acquires the image in which each of the region marker information of the lesion and the region marker information of the important tissue is set, and calculates the angle of the biopsy needle 410 for insertion of the biopsy needle 410 into the lesion based on the movable range of the biopsy needle 410 and the region marker information. This allows the user to easily perform an operation of inserting the biopsy needle 410 into the lesion while preventing the biopsy needle 410 from reaching the important tissue.

Figure 22:
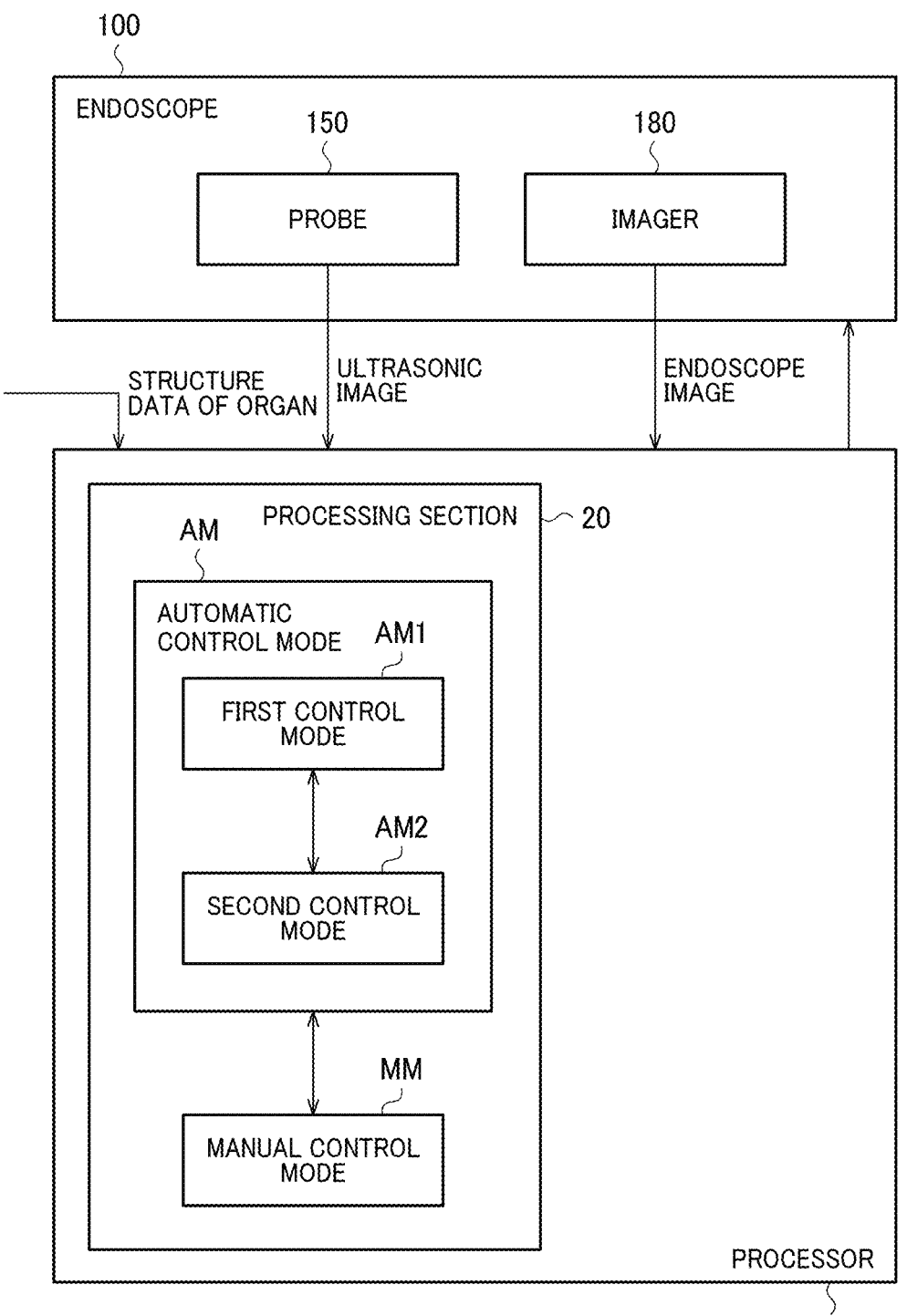
FIG. 22 is a diagram for describing another configuration example of the endoscope system.

For example, the endoscope system 1 of the present embodiment may be further capable of operating in the manual control mode MM. That is, as illustrated in a configuration example in FIG. 22, for example, the processing section 20 functions as a mode switching control section that operates the endoscope 100 in either the automatic control mode AM or the manual control mode MM. Additionally, when operating the endoscope 100 in the automatic control mode AM, the processing section 20 functions as a mode switching control section that operates the endoscope 100 in either the first control mode AM1 or the second control mode AM2.

Figure 23:
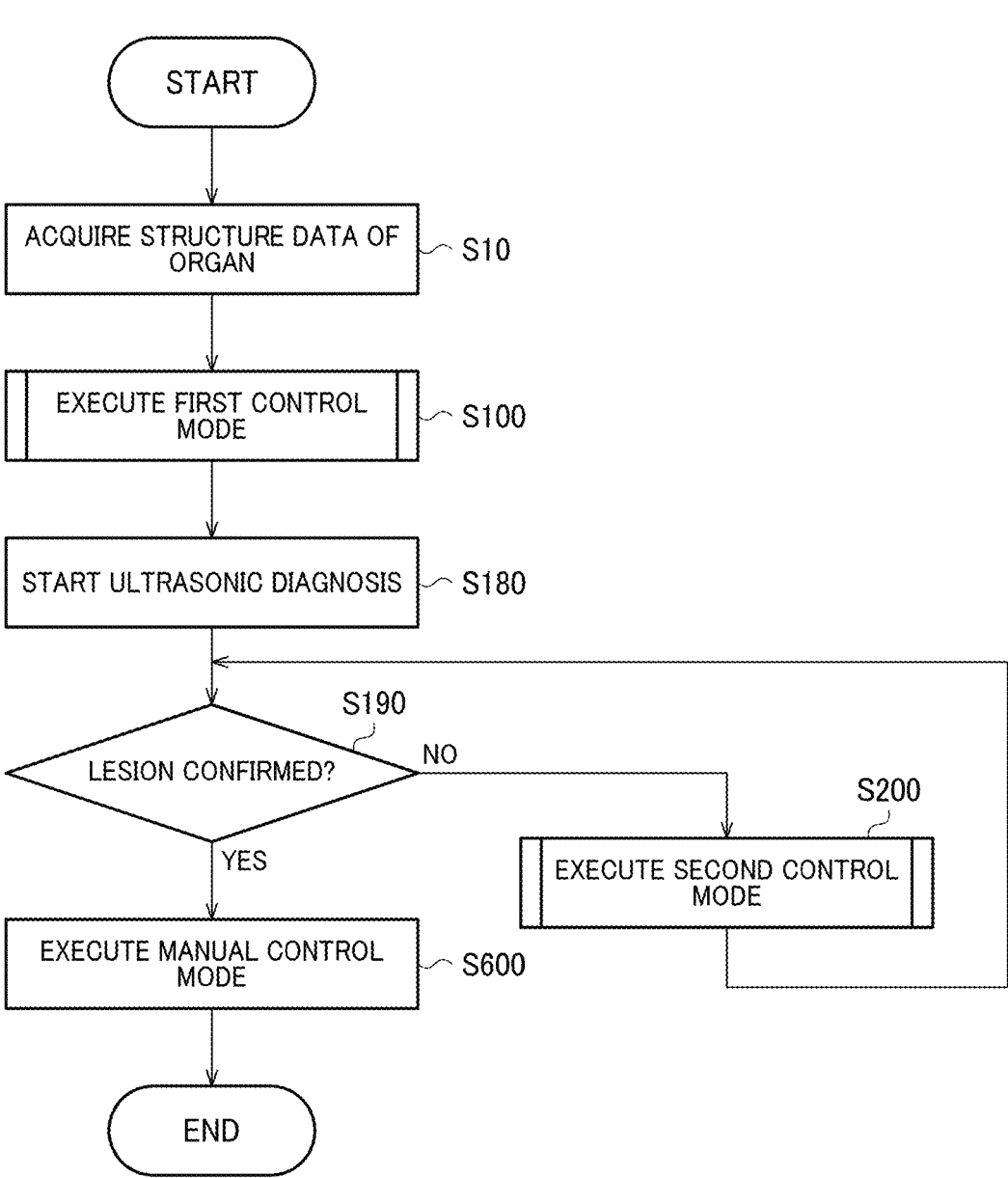
FIG. 23 is a flowchart describing another processing example of the method according to the present embodiment.

In this case, the processing example in FIG. 6 may be modified into a processing example described in a flowchart in FIG. 23. The processor 10 performs steps S100, S110, and S180 similarly to the flowchart in FIG. 6. Then, if determining that the lesion can be confirmed on the ultrasonic image (YES in step S190), the processor 10 switches the operation mode to the manual control mode MM and operates the endoscope 100 (step S600). In contrast, if determining that the lesion cannot be confirmed on the ultrasonic image (NO in step S190), the processor 10 switches the operation mode to the second control mode AM2 and operates the endoscope 100 (step S200). The processor 10 then performs processing of correcting the probe position or the like in the second control mode AM2 as described above with reference to FIG. 19 or the like, and thereby performs step S190 again. Since the probe position is corrected accordingly, the processor 10 determines that a result is YES in step S190 again, and performs the above-mentioned step S600.

In the manual control mode MM, for example, the user performs a manual operation to perform a treatment for inserting the biopsy needle 410 into the lesion. This allows the user to carefully perform an operation of inserting the biopsy needle 410 into the lesion. The processor 10 in the endoscope system 1 of the present embodiment controls the probe position in the second control mode AM2, and thereafter switches to the manual control mode MM for controlling the probe position (step S200, YES in step S190, and step S600). With this processing, it becomes possible to perform an appropriate treatment in a state where the probe 150 is arranged at an appropriate position. For example, in a case where a manipulation that requires carefulness such as insertion of the biopsy needle 410 into the lesion is included in the EUS-FNA, a manual operation can be performed according to the determination of the user. In this regard, application of the method of the present embodiment allows the endoscope 100 to operate differently between the automatic control mode AM and the manual control mode MM depending on a situation. With this configuration, it becomes possible to proceed with the treatment in an appropriate operation mode.

Figure 24:
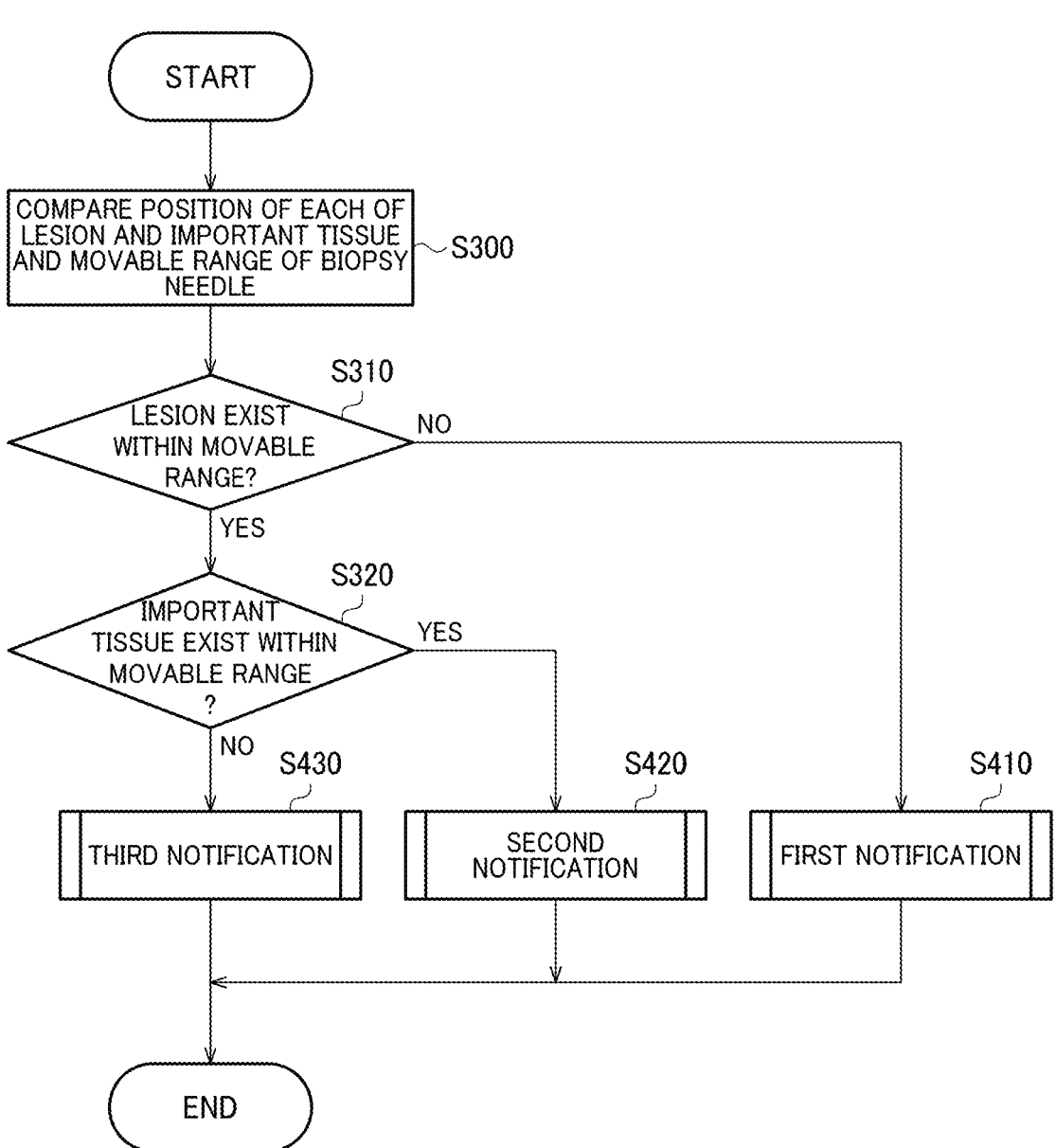
FIG. 24 is a flowchart describing a processing example of presentation processing to present operation support information.

In step S200, the processor 10 may be capable of presenting operation support information required to insert the biopsy needle 410. FIG. 24 is a flowchart corresponding to part of step S200 describing presentation processing for presenting the operation support information for operating the endoscope 100. That is, for example, the flow in FIG. 24 is added between step S230 and step S500 in FIG. 20, whereby presentation of the support information can be implemented. In this manner, in the second control mode AM2, the processor 10 in the endoscope system 1 of the present embodiment performs the presentation processing for presenting the operation support information for operating the endoscope 100 to the user based on the calculated angle and depth of the biopsy needle 410. This can reduce a work burden on the user to insert the biopsy needle 410 into the lesion.

The processor 10 in FIG. 24 compares the position of each of the lesion and the important tissue and the movable range of the biopsy needle 410 (step S300). If determining that the lesion does not exist in the movable range (NO in step S310), the endoscope system 1 performs first notification (step S410), and ends the flow. In contrast, if determining that the lesion exists within the movable range (YES in step S310), the endoscope system 1 determines whether or not the important tissue exists within the movable range (step S320). If determining that the important tissue exists in the movable range (YES in step S320), the endoscope system 1 performs second notification (step S420), and ends the flow. If determining that the important tissue does not exist in the movable range (NO in step S320), the endoscope system 1 performs third notification (step S430), and ends the flow.

Figure 25:
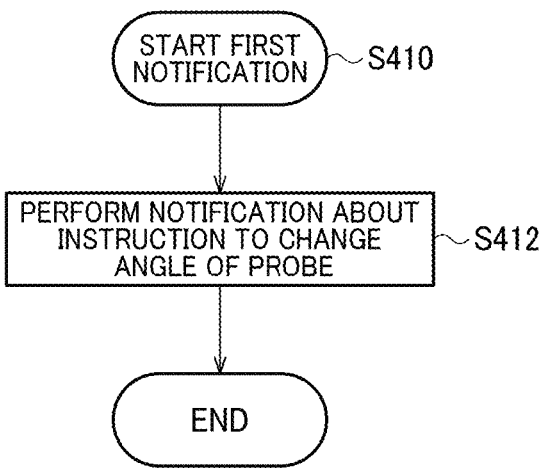
FIG. 25 is a flowchart describing a processing example of first notification.
Figure 26:
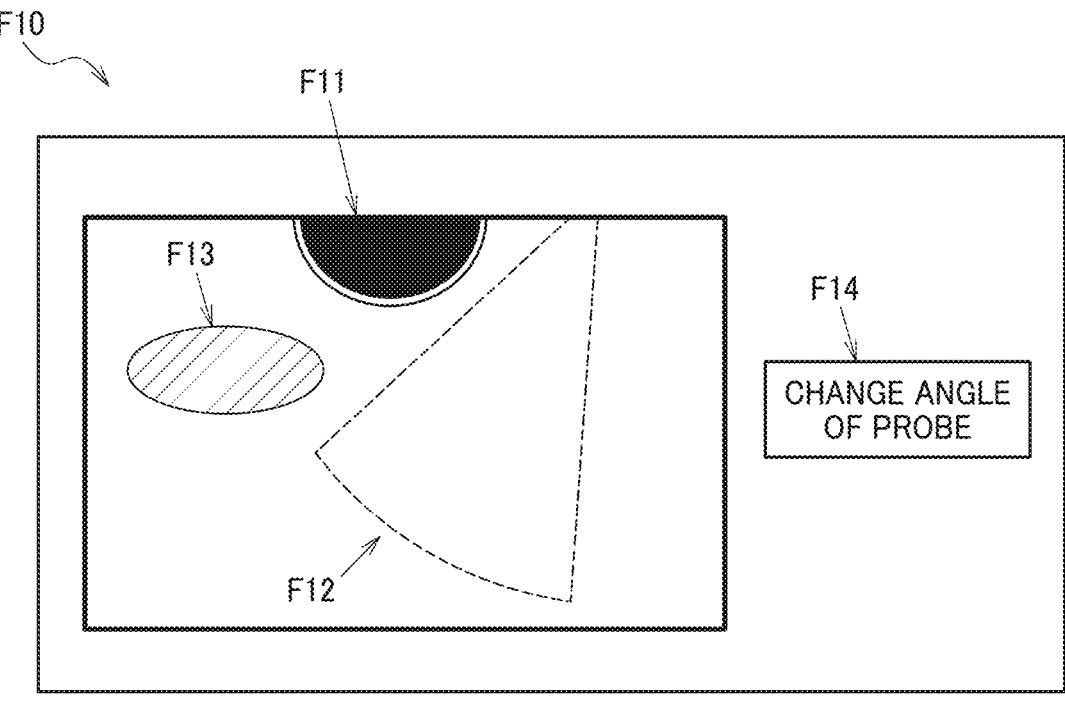
FIG. 26 is a diagram for describing a notification example of the first notification.

The first notification (step S410) is, specifically, to notify an instruction for changing the angle of the probe 150 as described in a flowchart in FIG. 25 (step S412). For example, assume that an ultrasonic image indicated by F11 is displayed on a screen indicated by F10 in FIG. 26. A movable range image indicated by F12 and region marker information indicated by F13 are displayed in the ultrasonic image indicated by F11. Assume that the region marker information indicated by F13 is region marker information corresponding to the lesion.

Since the movable range image indicated by F12 is not superimposed on the region marker information indicated by F13, the endoscope system 1 executes step S412. With this processing, for example, a message indicated by F14 is displayed on the screen indicated by F10. In this case, for example, the user performs an operation of curving the curved portion 102 in an upper direction on the paper, whereby the movable range image indicated by F12 is superimposed on the region marker information of the lesion indicated by F13. In this manner, the processor 10 in the endoscope system 1 of the present embodiment determines whether the lesion is included in the movable range in the second control mode AM2. In a case where the lesion is not included in the movable range, the processor 10 outputs instruction information to change the angle of the distal end portion 130 of the endoscope 100. With this processing, in a case where the lesion is not included in the movable range of the biopsy needle 410, the user can recognize that he/she can perform appropriate handling by changing of the angle of the probe 150.

Figure 27:
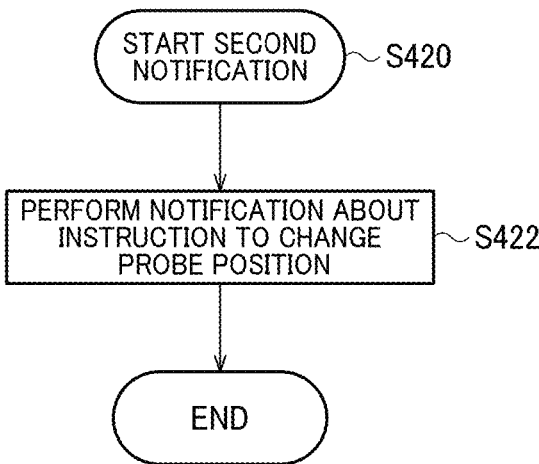
FIG. 27 is a flowchart describing a processing example of second notification.
Figure 28:
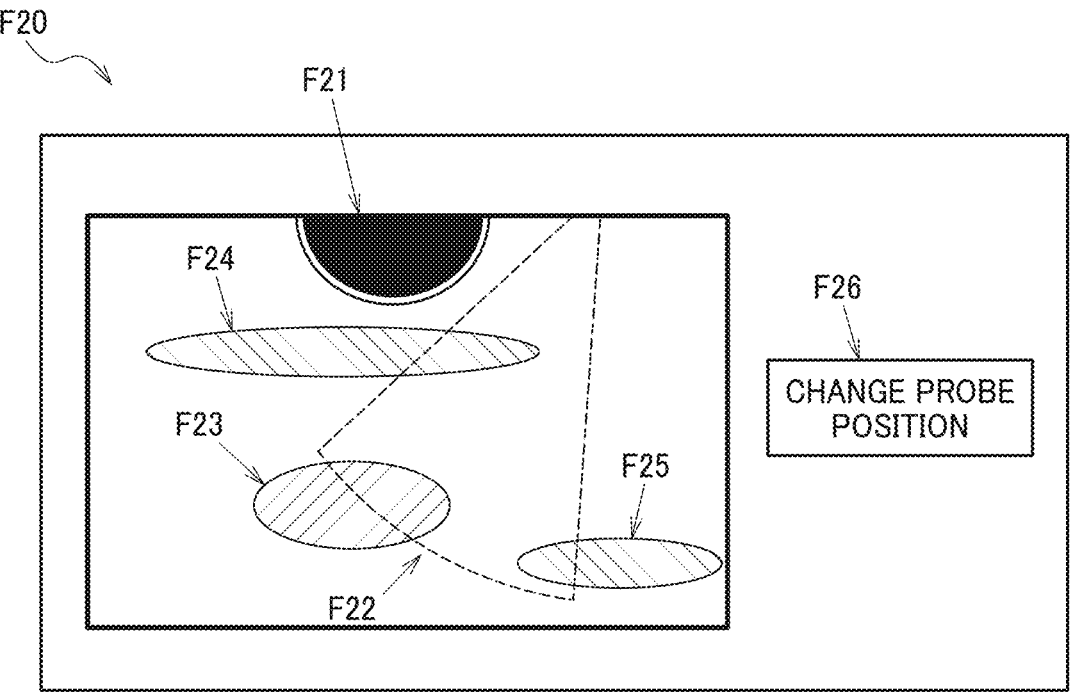
FIG. 28 is a diagram describing a notification example of the second notification.

The second notification (step S420) is, specifically, to notify an instruction for changing the position of the probe 150 as described in a flowchart in FIG. 27 (step S422). For example, assume that an ultrasonic image indicated by F21 is displayed on a screen indicated by F20 in FIG. 28. A movable range image indicated by F22, region marker information indicated by F23, region marker information indicated by F24, and region marker information indicated by F25 are displayed in the ultrasonic image indicated by F21. Assume that the region marker information indicated by F23 mentioned herein is the region marker information corresponding to the lesion, and each of the region marker information indicated by F24 and the region marker information indicated by F25 is region marker information corresponding to the important tissue.

Since the movable range image indicated by F22 is superimposed on the region marker information indicated by F23, it means a situation in which the biopsy needle 410 can be inserted into the lesion by being projected. However, the movable range image indicated by F22 is also superimposed on the region marker information indicated by F24 and the region marker information indicated by F25. Particularly, the region marker information indicated by F24 is located between a projection position of the biopsy needle 410 and the region marker information indicated by F23. If the biopsy needle 410 is projected under such a situation, the biopsy needle 410 in inserted into the important tissue, and there is a possibility that the important tissue is damaged.

Under such a situation, the endoscope system 1 executes step S422. With this processing, for example, a message indicated by F26 is displayed on the screen indicated by F20. Under a situation in FIG. 28, unlike the situation in FIG. 26, there is a case where it is impossible to superimpose only the region marker information corresponding to the lesion on the movable range image even if the angle of the probe 150 is changed. To address this, the processor 10 performs notification indicated by F26 to prompt the user to retreat the insertion portion 110 once and change an approach method with respect to the lesion. Therefore, in the second control mode AM2, the processor 10 in the endoscope system 1 of the present embodiment determines whether or not the important tissue is included between the projection position of the biopsy needle 410 and the lesion. If the important issue is included between the projection position of the biopsy needle 410 and the lesion, the processor 10 outputs instruction information to change the position of the endoscope 100. With this processing, in a case where the important tissue is included between the projection position of the biopsy needle 410 and the lesion, the user can recognize that it is difficult to project the biopsy needle 410 unless the approach method for causing the probe 150 to approach the lesion is changed. This allows the user to more appropriately perform the treatment using the biopsy needle 410.

Figure 29:
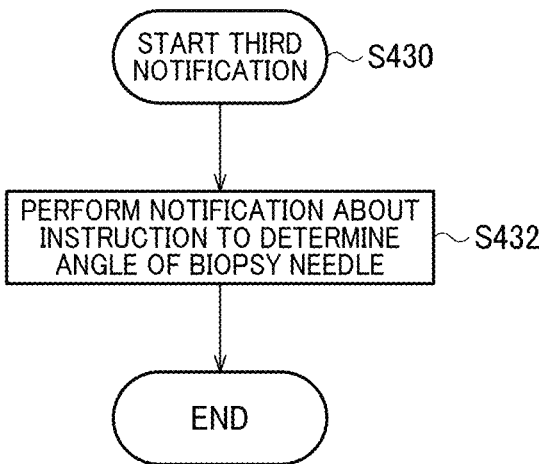
FIG. 29 is a flowchart describing a processing example of third notification.
Figure 30:
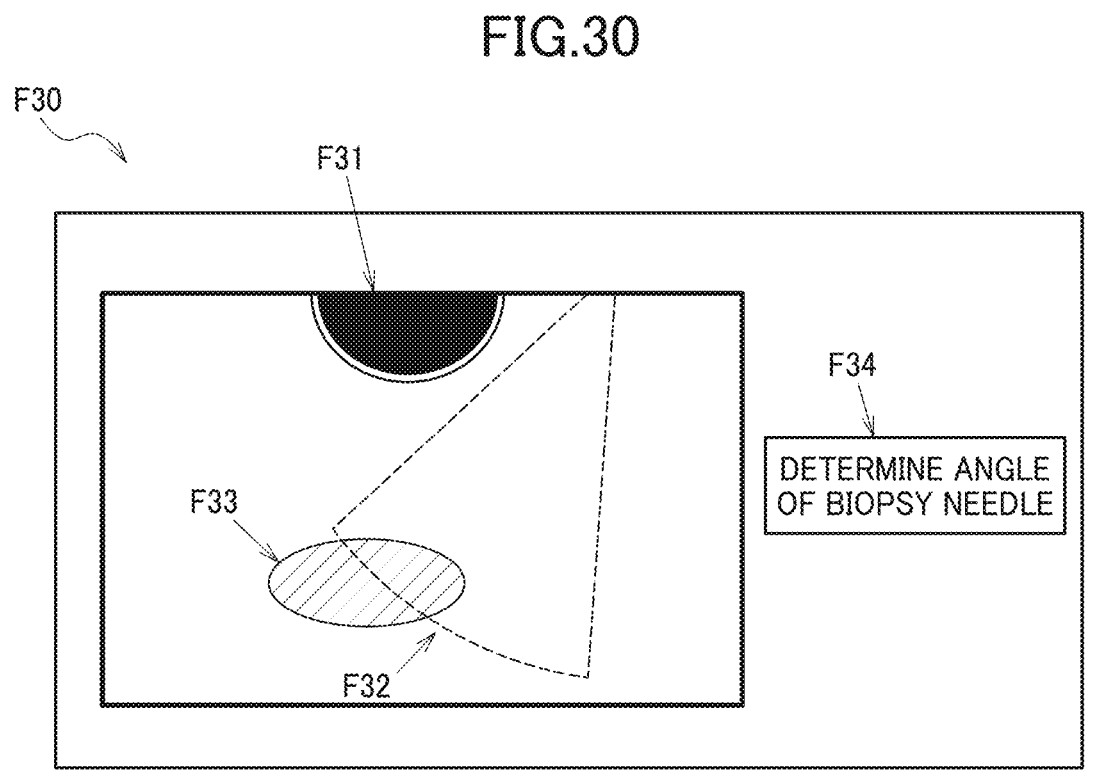

The third notification (step S430) is, specifically, to prompt the user to determine the angle of inserting the biopsy needle 410 as described in a flowchart in FIG. 29 (step S432). For example, assume that an ultrasonic image indicated by F31 is displayed on a screen indicated by F30 in FIG. 30. A movable range image indicated by F32 and region marker information indicated by F33 are displayed in the ultrasonic image indicated by F31. Assume that the region marker information indicated by F33 is the region marker information corresponding to the lesion.

Since the movable range image indicated by F32 is superimposed on the region marker information indicated by F33, it means a situation in which the biopsy needle 410 can be inserted into the lesion by being projected. Under a situation illustrated in FIG. 30, unlike the situation illustrated in FIG. 28, the movable range image indicated by F32 and the region marker information corresponding to the important tissue are not superimposed on each other. Thus, it is in a situation where the biopsy needle 410 can be inserted into the lesion by being projected without causing a damage on the important tissue. Under such a situation, the endoscope system 1 executes step S130. With this processing, for example, a message that the angle of the biopsy needle 410 needs to be determined is displayed on the screen indicated by F30 as indicated by F34. Thereafter, the processor 10 determines that a result is YES in step S190 and determines the angle of the biopsy needle 410 in step S500 in FIG. 20, the biopsy needle 410 is inserted into the lesion in the manual control mode MM in step S600 in FIG. 23, and a desired cellular tissue is collected. That is, in the second control mode AM2, the processor 10 in the endoscope system 1 of the present embodiment determines whether or not the lesion and the important tissue are included in the movable range. If the lesion is included in the movable range and the important tissue is not included in the movable range, the processor 10 outputs instruction information to insert the biopsy needle 410 into the lesion. This allows the user to recognize that it is in a situation where there is no problem if the biopsy needle 410 is projected.

Note that part of the processing in FIG. 24 may be combined with the processing in FIG. 23. For example, the processing in step S310 and the processing in step S320 in FIG. 24 may be replaced by step S190 in FIG. 23. In this case, a case where it is determined as YES in step S310 and it is determined as NO in step S320 is only required to be a case where it is determined as YES in step S190. For example, as described above, it is not necessarily appropriate to switch to the manual control mode MM in a case where the lesion and the important tissue are both located within the range of the movable range image. In this regard, in a case where the lesion and the important tissue are both located within the range of the movable range image, the processor 10 determines that a result is NO in step S190 and is thereby capable of prompting the user to change the probe position. This allows the endoscope system 1 to support the user to perform a more appropriate treatment.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, components in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

The invention claimed is:

1. A processing apparatus comprising:
a processor comprising hardware, the processor being configured to:
acquire structure data of an organ;
acquire an endoscope image from an imager of an endoscope;
acquire an ultrasonic image from a probe of the endoscope;
automatically control advancement, retraction, and angular adjustment of a probe position of the endoscope based on the structure data and a distal end position information of the endoscope in a first control mode; and
automatically control the probe position based on the ultrasonic image in a second control mode.

2. The processing apparatus of claim 1, wherein, the distal end position information is obtained based on the endoscope image.

3. The processing apparatus of claim 1, wherein, in the second control mode, the processor is configured to automatically control the probe position based on the structure data and the ultrasonic image.

4. The processing apparatus of claim 1, wherein the processor is configured to control the probe position in the first control mode, and thereafter control the probe position in the second control mode.

5. The processing apparatus of claim 1, wherein the processor is configured to control the probe position in the second control mode, and thereafter switches the second control mode to a manual control mode to manually control the probe position.

6. The processing apparatus of claim 1, wherein automatically controlling advancement, retraction, and angular adjustment of the probe position of the endoscope in the first control mode comprises:
estimating a target position of the probe based on the structure data, and
automatically controlling the probe position to the estimated target position based on the endoscope image.

7. The processing apparatus of claim 1, wherein, automatically controlling the probe position based on the ultrasonic image in the second control mode comprises:
automatically controlling the probe position based on a treatment target position identified based on the ultrasonic image.

8. The processing apparatus of claim 7, wherein the processor is configured to correct the probe position estimated in the first control mode based on the treatment target position.

9. The processing apparatus of claim 1, wherein, in the second control mode, the processor is configured to calculate an angle of a biopsy needle to insert the biopsy needle into a lesion based on a movable range of the biopsy needle.

10. The processing apparatus of claim 9, wherein, in the second control mode, the processor is configured to present operation support information for the endoscope to a user based on the calculated angle of the biopsy needle and a depth of the biopsy needle.

11. The processing apparatus of claim 9, wherein in the second control mode, the processor is configured to:
acquire an image in which region marker information of the lesion is set, and
calculate an angle of the biopsy needle to insert the biopsy needle into the lesion based on the movable range of the biopsy needle and the region marker information.

12. The processing apparatus of claim 9, wherein in the second control mode, the processor is configured to:

acquire an image in which region marker information of each of the lesion and an important tissue is set, and calculate an angle of the biopsy needle to insert the biopsy needle into the lesion based on the movable range of the biopsy needle and the region marker information.

13. The processing apparatus of claim 9, wherein in the second control mode, the processor is configured to:

determine whether or not the lesion is included in the movable range, wherein the lesion is not included in the movable range, output instruction information to change an angle of a distal end portion of the endoscope.

14. The processing apparatus of claim 9, wherein in the second control mode, the processor is configured to:

determine whether or not the lesion and an important tissue are included in the movable range, wherein the lesion is included in the movable range and the important tissue is not included in the movable range, output instruction information to insert the biopsy needle into the lesion.

15. The processing apparatus of claim 9, wherein in the second control mode, the processor is configured to:

determine whether or not an important tissue is included between a projection position of the biopsy needle and the lesion, wherein the important tissue is included between the projection position of the biopsy needle and the lesion, output instruction information to change a position of the endoscope.

16. The processing apparatus of claim 1, wherein the automatically controlling the probe position in the first control mode is controlling an actuator to control the probe position.

17. The processing apparatus of claim 1, wherein the automatically controlling the probe position in the second control mode is controlling an actuator to control the probe position.

18. An endoscope system comprising:

a processor comprising hardware, the processor being configured to:

acquire structure data of an organ;

acquire an endoscope image from an imager of an endoscope;

acquire an ultrasonic image from a probe of the endoscope;

automatically control advancement, retraction, and angular adjustment of a probe position of the endoscope based on the structure data and distal end position information of the endoscope in a first control mode; and automatically control the probe position based on the ultrasonic image in a second control mode, wherein, in the second control mode, the processor is configured to calculate an angle of a biopsy needle to insert the biopsy needle into a lesion based on a movable range of the biopsy needle;

a memory that stores a trained model trained so as to output region marker information of a detection target in the ultrasonic image;

wherein, in the second control mode, the processor is configured to detect at least one of the region marker information of the lesion or the region marker information of an important tissue based on the ultrasonic image and the trained model.

19. A control method comprising:

acquiring structure data of an organ;

acquiring an endoscope image from an imager of an endoscope;

acquiring an ultrasonic image from a probe of the endoscope;

automatically controlling advancement, retraction, and angular adjustment of a probe position of the endoscope based on the structure data and a distal end position information of the endoscope in a first control mode; and automatically controlling the probe position based on the ultrasonic image in a second control mode.

20. The control method of claim 19, wherein automatically controlling advancement, retraction, and angular adjustment of a probe position of the endoscope in the first control mode comprises:

obtaining the distal end position information based on the endoscope image, and automatically controlling the probe position based on the obtained distal end position information and the structure data.

* * * * *